US007970581B2

(12) United States Patent
Young et al.

(10) Patent No.: US 7,970,581 B2
(45) Date of Patent: Jun. 28, 2011

(54) METHODS OF CALCULATING DIFFERENCES OF BINDING AFFINITIES BETWEEN CONGENERIC PAIRS OF LIGANDS BY WAY OF A DISPLACED SOLVENT FUNCTIONAL

(75) Inventors: Thomas Young, New York, NY (US); Robert Abel, Davie, FL (US); Richard A. Friesner, New York, NY (US); Bruce J. Berne, Irvington, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 12/791,493

(22) Filed: Jun. 1, 2010

(65) Prior Publication Data

US 2010/0241412 A1    Sep. 23, 2010

Related U.S. Application Data

(62) Division of application No. 11/982,783, filed on Nov. 5, 2007, now Pat. No. 7,756,674.

(60) Provisional application No. 60/953,764, filed on Aug. 3, 2007.

(51) Int. Cl.
*G01N 33/48* (2006.01)

(52) U.S. Cl. ............ 702/172; 702/19; 702/27; 702/136; 374/45

(58) Field of Classification Search .................... 702/19, 702/27, 130, 172, 179, 134, 136; 374/5, 374/45; 703/11
See application file for complete search history.

(56) References Cited

U.S. PATENT DOCUMENTS

| 6,193,413 | B1 | 2/2001 | Lieberman | |
|---|---|---|---|---|
| 6,226,603 | B1 * | 5/2001 | Freire et al. | 703/11 |
| 6,230,102 | B1 * | 5/2001 | Tidor et al. | 506/2 |
| 6,735,530 | B1 | 5/2004 | Guarnieri | |
| 6,772,073 | B2 | 8/2004 | Freire et al. | |
| 2004/0215400 | A1 | 10/2004 | Slovic et al. | |
| 2007/0061118 | A1 | 3/2007 | Friesner et al. | |
| 2008/0312840 | A1 | 12/2008 | Desmet et al. | |

OTHER PUBLICATIONS

Jacobs et al., "Elucidating Protein Thermodynamics from the Three-Dimensional Structure of the Native State Using Network Rigidity", Biophysical Journal, vol. 88, Feb. 2005, pp. 903-915.*
Barillari et al., "Classification of Water Molecules in Protein Binding Sites", J. Am. Chem. Soc., 129: 2577-2587 (2007).

(Continued)

*Primary Examiner* — John H Le
(74) *Attorney, Agent, or Firm* — Baker Botts LLP

(57) ABSTRACT

Described is a technique to exhaustively enumerate the thermodynamic properties of the water molecules solvating the active site of a protein in its apostate and calculate the relative binding affinities of congeneric compounds that bind to this protein. The subject matter includes sampling the configurations of the solvating water in the active site; extracting the thermodynamic information about the solvating water from these configurations by clustering the observed water configurations into regions of high water occupancy (e.g., "hydration sites"), computing the average system interaction energies of water molecules occupying the various hydrations sites, computing excess entropies of water molecules occupying the hydration sites; constructing a 3 dimensional hydration thermodynamics map of the protein active site; and computing relative binding affinities of congeneric ligands based on the principle that tighter binding ligands can displace more entropically structured and energetically depleted hydration sites from the active site into the bulk fluid.

14 Claims, 17 Drawing Sheets

OTHER PUBLICATIONS

Silberstein et al., "Computational Methods for Functional Site Identification Suggest a Substrate Access Channel in Transaldolase", *Genome Informatics*, 17(1): 13-22 (2006).

Dennis et al., "Computational mapping identifies the binding sites of organic solvents on proteins", *Proc. Nat. Acad Sci.*, 99(7): 4290-4295 (2002).

Clark, et al., "Grand Canonical Monte Carlo Simulation of Ligand-Protein Binding", *J. Chem. Inf. Model.*, 46: 231-242 (2006).

Gilson, et al., 2007, "Calculation of Protein-Ligand Binding Affinities," <http://arjournals.annualreviews.org/doi/abs/10.1146/annurev.biophys.36.040306.132550> retrieved on [Nov. 21, 2008].

Notice of Allowance issued on Mar. 3, 2010 in U.S. Appl. No. 11/982,783.

Response filed on Jan. 6, 2010 in U.S. Appl. No. 11/982,783.

Non-final rejection issued on Oct. 1, 2009 in U.S. Appl. No. 11/982,783.

Non-final rejection issued Sep. 17, 2010 in U.S. Appl. No. 11/791,448.

Response to non-final rejection, filed on Dec. 15, 2010, in U.S. Appl. No. 11/791,448.

\* cited by examiner

US 7,970,581 B2

METHODS OF CALCULATING DIFFERENCES OF BINDING AFFINITIES BETWEEN CONGENERIC PAIRS OF LIGANDS BY WAY OF A DISPLACED SOLVENT FUNCTIONAL

CROSS REFERENCE TO RELATED APPLICATIONS

This application is a divisional of Ser. No. 11/982,783, filed Nov. 5, 2007 now U.S. Pat. No. 7,756,674, which claims priority to U.S. Provisional Application Ser. No. 60/953,764, filed on Aug. 3, 2007, which is incorporated by reference herein, and from which priority is claimed.

STATEMENT REGARDING FEDERALLY SPONSORED RESEARCH

The subject matter described herein was funded in part by federal grants: subcontract NIH GM52018, NIH GM43340, UMD UMARY Z477901, and NSF CHE 06 13401. The United States Government may have certain rights herein.

BACKGROUND

Understanding the underlying physics of the binding of small molecule ligands to protein active sites is one objective of computational chemistry and biology. While a wide range of techniques exist for calculating binding free energies, ranging from techniques that should be accurate in principle (e.g., free energy perturbation (FEP) theory) to relatively simple approximations based on empirically derived scoring functions, no completely satisfactory and robust approach has yet been developed. Furthermore, physical insight into the sources of binding affinity can be important for computing accurate numbers and can be valuable in many areas (e.g., the design of pharmaceutical candidate molecules).

It is widely believed that displacement of water molecules from the active site by the ligand is a major source of binding free energy. Water molecules solvating protein active sites are often entropically unfavorable due to the orientational and positional constraints imposed by the protein surface, or energetically unfavorable due to the water molecule's inability to form a full complement of hydrogen bonds when solvating the protein surface. This leads to free energy gains when a ligand that is suitably complementary to the active site displaces these waters into bulk solution, thus providing a relatively more favorable environment. FEP techniques can compute these free energy gains explicitly (within the accuracy of the force field used in the simulations) but are computationally expensive.

This computational expense has been a barrier to the adoption of FEP based techniques since, in some situations, computational techniques to predict protein-ligand binding free energies must take less wall clock time than synthesizing the small molecule and experimentally testing the binding affinity if these techniques are to have value, (e.g., in an industrial drug design setting). This demand for speed has motivated a broad use of continuum theories of hydration within empirical scoring functions to describe the contributions of the solvent to the binding affinity of the complex. However, it is still an unsettled question as to whether or not these continuum solvation theories describe the underlying molecular physics with sufficient accuracy to reliably rank the binding affinities of a set of ligands for a given protein.

SUMMARY

Methods of calculating differences of binding affinities between congeneric pairs of ligands by way of a displaced solvent functional are described.

Some embodiments include procedures for enumerating local statistical thermodynamic properties of water solvating a receptor including (a) sampling configurations of the water solvating a receptor; (b) extracting thermodynamic information about the solvating water from the configurations including (i) automatically partitioning observed water configurations into hydration sites, (ii) computing average system interaction energies of water molecules occupying the hydration sites, and (iii) computing excess entropies of the water molecules occupying the hydration sites, and (c) enumerating the local statistical thermodynamic properties of water solvating the receptor. molecular dynamics simulations can be used to sample the configurations of the solvating water in the receptor. Monte Carlo techniques can also be used to sample the configurations of the solvating water in the receptor. The water configurations can automatically partitioned into hydration sites by clustering the water configurations into regions of high water occupancy. Orientational contributions to the excess entropy can be computed using a mixed quaternion/Euler angle technique. The receptor can be an active site of a protein.

Some embodiments include procedures for computing a binding affinity of a ligand for a receptor including (a) calculating local statistical thermodynamic properties of water molecules solvating the receptor; and (b) calculating free energy gain of displacement of solvent from the receptor by the ligand including (i) inserting the ligand into the receptor, (ii) algorithmically determining steric overlap of the ligand with the solvent, and (iii) calculating the free energy gain of the ligand sterically displacing the solvent based on the results of the algorithmically determining steric overlap of the ligand with the solvent and the thermodynamic properties of the displaced solvent. The procedure can further include (c) sampling configurations of the water solvating a receptor; (d) extracting thermodynamic information about the solvating water from the configurations including (i) automatically partitioning observed water configurations into hydration sites, (ii) computing average system interaction energies of water molecules occupying the hydration sites, and (iii) computing excess entropies of the water molecules occupying the hydration sites. The free energy gain for atoms of the ligand sterically displacing the solvent can be computed as a function of the thermodynamic properties of the solvent. The free energy gain for atoms of the ligand sterically displacing the solvent can be the excess chemical potential of the solvent as compared to bulk fluid. Enthalpic contribution to the free energy of a ligand atom displacing a hydration site is assigned as a constant where a value of the average system interaction energy exceeds a threshold. Entropic contribution to the free energy of a ligand atom displacing a hydration site is assigned as a constant where a value of the excess entropy exceeds a specified threshold. The parameters of constant gains upon displacement and threshold values are determined by optimizing against experimental data. The free energy gain is computed as the sum of (1) the output of the function of the thermodynamic properties of the solvent and (2) the excess chemical potential of the solvent as compared to bulk fluid.

Some embodiments include procedures where the free energy gain is computed as the sum of the enthalpic and entropic contribution of a ligand atom displacing a hydration site. Values for a particular receptor are optimized by using data for ligands binding to that receptor. Values for a class of receptors are optimized by fitting to data from a diverse set of receptor-ligand complexes. Some procedures further include (c) calculating a difference in binding free energy between two ligands, the difference corresponding to the difference in the free energy gain from water displacement. The ligands can be a congeneric pair. The ligands differ by deletions of atoms.

Some embodiments include procedures for constructing a 3 dimensional hydration thermodynamics map of a receptor including (a) calculating local statistical thermodynamic properties of water molecules solvating the receptor; and (b) visualizing the local statistical thermodynamic properties of the solvent as hydration sites against the backdrop of the receptor. Other embodiments further include (e) sampling configurations of the water solvating a receptor; and (d) extracting thermodynamic information about the solvating water from the configurations including (i) automatically partitioning observed water configurations into hydration sites, (ii) computing average system interaction energies of water molecules occupying the hydration sites, and (iii) computing excess entropies of the water molecules occupying the hydration sites. The hydration sites can be displayed against the backdrop of the receptor when the energetic and entropic properties are above or below one or more cutoff values. A color code can be used to represent the energetic and entropic properties of the displayed hydration sites. Other embodiments further include (e) visualizing a ligand in the receptor superimposed with the hydration sites.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
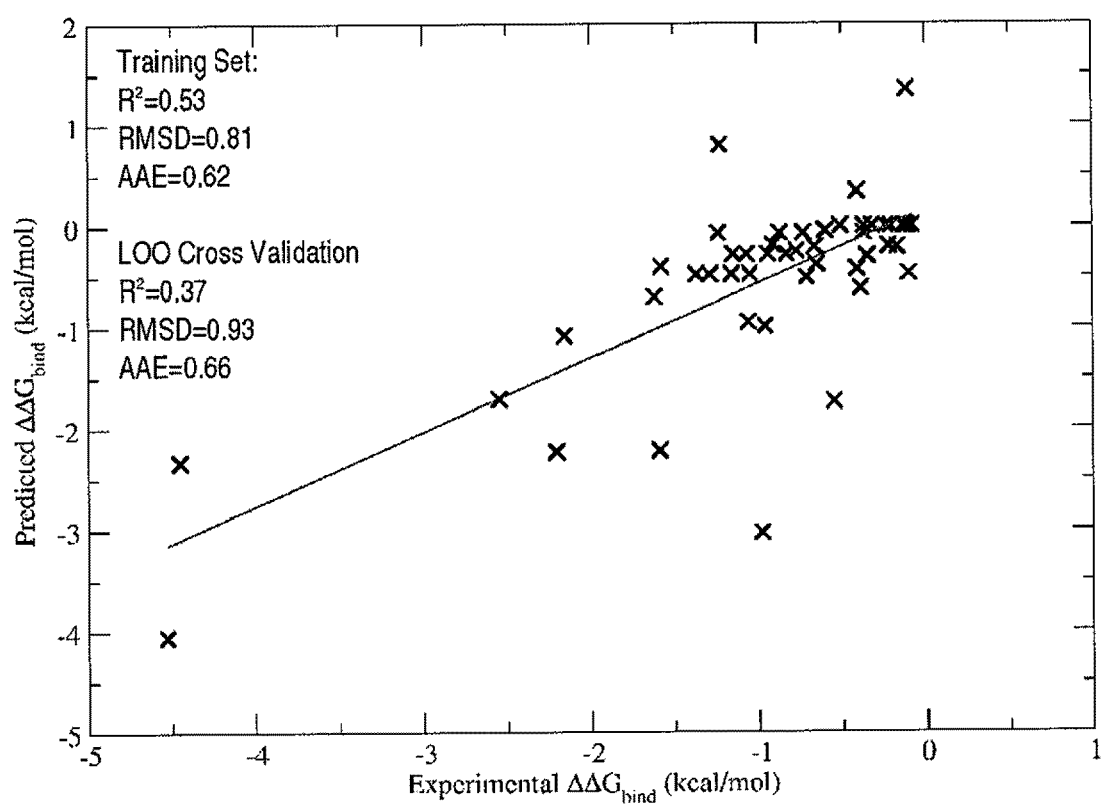
FIG. 1 is a depiction according to some embodiments of the described subject matter and depicts system interaction energies (E) and the excess entropic contributions to the free energy ($-TS^e$) of water molecules in the principal hydration sites of the factor Xa active site. The system interaction energy includes the average energy of interaction of the water molecules in a given hydration site with the rest of the system and the excess entropic contribution to the free energy is calculated from a truncated expansion of the excess entropy in terms of correlation functions. Those hydration sites that were expected to make large energetic contributions when evacuated by the ligand are circled in gray, those expected to make large entropic contributions are circled in green, and those expected to make both entropic and enthalpic contributions are circled in purple.

In one embodiment, a technique of directly computing the thermodynamic properties of water molecules solvating the active site of the apoprotein is described. In this embodiment, techniques have been applied to understand the thermodynamics of ligand binding in factor Xa (fXa) and cyclin dependent kinase 2 (CDK2). FXa can be an important drug target in the thrombosis pathway and CDK2 can be an target for next generation anticancer treatments. Techniques involve automatically partitioning the solvent density by way of a clustering technique to build a map of water occupancy in the protein active site, and assigning chemical potentials to the water sites using an expansion of the entropy in terms of correlation functions. Another embodiment includes a semi empirical extension of the model which enables computation of free energy differences ($\Delta\Delta G$ values) for selected pairs of fXa and CDK2 ligands from merely a single explicitly solvated molecular dynamics simulation of a ligand-free protein structure. Initial results suggest that any protein structure, by which results can be examined, is acceptable as long as it is compatible with the congeneric ligand pairs being studied). In some embodiments, the free energy differences calculated from the semi empirical model are shown to correlate well with experimental data ($R^2=0.81$ for fXa and $R^2=0.53$ for CDK2) via the use of three adjustable parameters. In some example simulations, 31 pairs of fXa ligands and 47 pairs of CDK2 ligands were investigated using data from a single 10 ns MD simulation of each receptor, illustrating the high computational efficiency of the described techniques. Furthermore, the solvent chemical potential map produced here appears to elucidate features of the known fXa and CDK2 structure activity relationships (SARs), and can provide a useful starting point for efforts to design novel compounds. An effort to calculate absolute binding free energies for highly diverse ligands can display less accuracy and some over fitting (as would be expected, since the displacement of water molecules is not the single factor determining binding affinity), but still shows a significant correlation with experimental data for this data set.

One embodiment provides a technique to exhaustively enumerate the thermodynamic properties of the water molecules solvating the active site of a protein in its apostate and calculate the relative binding affinities of congeneric compounds that bind to this protein. This technique includes (a) sampling the configurations of the solvating water in the active site with molecular dynamics simulation; (b) extracting the thermodynamic information about the solvating water from these configurations by (i) automatically partitioning the observed water configurations by way of clustering the observed water configurations into regions of high water occupancy (e.g., "hydration sites"), (ii) computing the average system interaction energies of water molecules occupying the various hydrations sites, (iii) computing excess entropies of the water molecules occupying the hydration sites; (c) constructing a 3-dimensional hydration thermodynamics map of the protein active site; and (d) computing the relative binding affinities of congeneric ligands based on the principle that tighter binding ligands will displace more entropically structured and energetically depleted hydration sites from the active site into the bulk fluid.

The sampling of the configurations of the solvating water can be performed by some technique that can reproduce the thermal ensemble of the water molecules hydrating the protein active site. In some embodiments, explicitly solvated molecular dynamics simulations of the protein can be used to build this ensemble. In some embodiments, Metropolis Monte Carlo or replica exchange molecular dynamics simulations can also be used.

In one embodiment, the extraction of the thermodynamic information of the solvating water is performed by a technique of applying an expansion of the excess entropy in terms of correlation functions to the active site of a protein, where the water molecules can freely exchange with the bulk fluid. Because the water molecules were free to exchange with the bulk fluid, a rigorous definition of the active site volume was constructed. This allows unambiguous determination of when a water molecule is within the active site and when it is not. This rigorous definition can be constructed, by way of example, according to the techniques described in the experiments. This definition allowed the extraction of the coordinates and properties of all water molecules found in the active site of the protein during the simulation. This distribution of water molecules was assumed to be the equilibrium distribution and will be referred to, in some embodiments, as the active site solvent density distribution.

Although the difficulty posed by waters exchanging with the bulk fluid is alleviated by definition of the active site, the inhomogenous topography of the protein surface made the orientational distributions of the water molecules dependent on their position within the active site. Some embodiments include a procedure to partition the active site volume into small subvolumes, known in some embodiments as hydration sites (the description of this term is not limited thereto), and treated the angular distributions as independent of position in these subvolumes. Identification of the subvolumes was accomplished by applying a clustering algorithm to partition the solvent density distribution into a set of non-overlapping high water occupancy 1 Å radius spheres. This algorithm cycled through the positions of the oxygen atom of every water molecule found in the active site solvent density distribution and found the position that has the greatest number of water neighbors within a 1 Å radius. This position, in some embodiments, can be known as a hydration site and the hydration site can be removed it and all of the oxygen positions within 1 Å of it from the solvent density distribution. This process was then repeated, cycling through the remaining positions. This loop was terminated when the clustering algorithm identified a hydration site with a water-oxygen occupancy less than twice the expected value of a 1 Å radius sphere in the bulk fluid. These hydration sites are defined subvolumes of the active site and have good convergence properties for the expansion of the excess entropy in terms of correlation functions since they have sparse water density toward the edges of the clusters.

In some embodiments, it was defined that the system interaction energy ($E_{hs}$) of each hydration site is the average energy of interaction of the water molecules in a given hydration site with the rest of the system. This quantity was extracted from the molecular dynamics simulations of the solvated aporeceptor.

The partial excess entropy ($S^e$) of each hydration site was also computed by numerically integrating the inhomogeneous solvation theory expansion of the entropy in terms of orientational and spatial correlation functions. In this example, contributions from the first order term for each hydration site were included:

$$S^e = -\frac{k_b \rho_w}{\Omega} \int g_{sw}(r, \omega) \ln(g_{sw}(r, \omega)) dr d\omega \approx \qquad (1)$$
$$-k_b \rho_w \int g_{sw}(r) \ln(g_{sw}(r)) dr - \frac{k_b N_W^V}{\Omega} \int g_{sw}(\omega) \ln(g_{sw}(\omega)) d\omega$$

where r and ω are the Cartesian position and Euler angle orientation of a water molecule, $g_{sw}(r, \omega)$ is the 1-body distribution of the water (w) at r and ω in the fixed reference frame of the solute protein (s), $\rho_w$ is the density of bulk water, $k_b$ is the Boltzmann constant, Ω is the total orientational space accessible to a water molecule, and $N_W^V$ is total number of water oxygens found within a given hydration site of volume V.

The computation of the translational one-body integral for each hydration site was performed by discretizing the spherical coordinate space of each hydration site into 0.03 Å bins along r, 15° bins along Θ, and 30° bins along Φ.

The integration of the rotational component of the one-body term throughout a subvolume V is performed semi analytically by way of a mixed quaternion/Euler angle formalism. Each water oxygen within the cluster is translated to a common reference point and the hydrogens are moved accordingly. The hydrogen to hydrogen mapping that allows for the smallest rotation of a water in the cluster are determined by a hydrogen to hydrogen distance criterion, i.e., $H_1$->$H_a$ and $H_2$->$H_b$ should be minimal. The quaternion maps $H_1$->$H_a$ using the rotational axis orthogonal to the $OH_1$ and $OH_a$ bond vectors. This rotation is applied and a second quaternion is determined that will rotate $H_2$->$H_b$ using the analogous orthogonal axis. These two quaternions are combined using the analytical combination rules to derive the single "master" quaternion that rotates $H_1$->$H_a$ and $H_2$->$H_b$ simultaneously. It should be noted that the calculation of this quaternion can be done in a single stage using the axis of rotation orthogonal to vectors $H_1 H_a$ and $H_2 H_b$. From the "master" quaternion, the three Euler angles that rotate a cluster water onto the reference water were analytically extracted. This process was repeated for all waters and the rotational correlation function was determined from the distribution of the Euler angles and used to numerically integrate the one-body rotational term using a 10° discretization.

The 3-dimension hydration thermodynamics map was constructed by plotting the locations of the hydration sites in space relative to the surface of the protein and color coding the hydration sites to represent their thermodynamic properties.

In some embodiments, computing the relative binding affinities of congeneric ligands from the information contained in this hydration thermodynamics map was based on the following physical concepts: (1) if a heavy atom of a ligand overlapped with a hydration site, it displaced the water from that site; and (2) the less energetically or entropically favorable the expelled water, the more favorable its contributions to the binding free energy. A hydration site would contribute to the binding free energy if its excess entropy or system interaction energy were beyond the fitted entropy and energy cutoff parameters $S_{co}$ and $E_{co}$, respectively. A flat reward was given for any hydration site that had excess entropies or system interaction energies that were beyond these values. The amplitude of the reward values, $S_{rwd}$ and $E_{rwd}$, were fit accordingly. A fit cutoff distance ($R_{co}$) was used to determine whether a heavy atom of the ligand displaced water from a hydration site. If the ligand heavy atom had the same position as the hydration site, the full value of $S_{rwd}$ and $E_{rwd}$ would be awarded. The reward was then linearly reduced to zero over the distance $R_{co}$. This scoring function was implemented as $$\Delta G_{lig} = \sum_{lig,hs} E_{rwd}\left(1 - \frac{\vec{r}_{lig} - \vec{r}_{hs}}{R_{co}}\right)\Theta(E_{hs} - E_{co})\Theta(R_{co} - |\vec{r}_{lig} - \vec{r}_{hs}|) - \quad (2)$$

$$T\sum_{lig,hs} S_{rwd}\left(1 - \frac{\vec{r}_{lig} - \vec{r}_{hs}}{R_{co}}\right)\Theta(S^e_{hs} - S_{co})\Theta(R_{co} - |\vec{r}_{lig} - \vec{r}_{hs}|)$$

where $\Delta G_{bind}$ was the predicted binding free energy of the ligand, $E_{hs}$ is the system interaction energy of a hydration site, $S^e_{hs}$ is the excess entropy of a hydration site, and $\Theta$ is the Heaviside step function. This implementation can be known, without limitation, to be the "displaced -solvent functional". Implementing this displaced-solvent functional was particularly simple since it is merely a sum over the ligand heavy atoms and a restricted sum over the entropically structured and energetically depleted hydration sites, with a linear function of the hydration-site-ligand-atom approach distance as its argument. Note that some hydration sites contributed in both the entropic and energetic sums. We also constructed a 3-parameter scoring function based on the same principles as the 5-parameter scoring function, where the value of $R_{co}$ was set to 2.8 Å and the values of $S_{rwd}$ and $E_{rwd}$ were forced to be equal. The parameterization of these terms can be accomplished, by way of example, according to the techniques described in the Experimental Details.

EXPERIMENTAL DETAILS

The present subject matter describes techniques to map the thermodynamic properties of the water molecules solvating the active site of a protein and techniques to compute the differences in binding affinity of congeneric ligands for the protein from this hydration thermodynamics information. In some embodiments, the configurations of the solvating water in the active site are sampled with molecular dynamics simulation, and from this molecular dynamics trajectory the subject matter describes an algorithm to extract the thermodynamic properties of all regions in the active site with high water occupancy. These high water occupancy regions can be referred to as, without limitation, "hydration sites." Energetic and entropic information for water molecules occupying these hydration sites are directly computed. In some embodiments, the subject matter includes a technique to display this hydration thermodynamics information visually as a map of the local chemical potential of water molecules solvating the active site. Some embodiments include an algorithm that can compute differences in binding affinity of congeneric ligands for the protein based on the physical principle that tighter binding ligands will evacuate water from more entropically structured and energetically depleted hydration sites.

In some embodiments, the present subject matter can be used to study the thermodynamics of ligand binding in factor Xa (fXa) and cyclin dependent kinase 2 (CDK2) (as shown by the example below). FXa can be an important drug target in the thrombosis pathway and CDK2 can be an attractive target for next generation anticancer treatments. This has led to active targeting of both these systems by the pharmaceutical industry. The free energy differences calculated from the semi empirical model are shown to correlate with experimental data ($R^2=0.81$ for FXa and $R^2=0.53$ for CDK2) via the use of three adjustable parameters. 31 pairs of fXa ligands and 47 pairs of CDK2 ligands were investigated using data from only a single 10 ns MD simulation of each receptor, illustrating a high computational efficiency of the techniques. Furthermore, the solvent chemical potential map produced here appears to elucidate features of the known fXa and CDK2 structure activity relationships (SAR), and can provide a useful starting point for efforts to design novel compounds. An effort to calculate absolute binding free energies for highly diverse ligands displays less accuracy and some over-fitting (as would be expected, since the displacement of water molecules is not the single factor determining binding affinity), but still shows a significant correlation with experimental data for this data set.

I. Application to the Test System Factor Xa

A. Structure Preparation and Simulation of Factor Xa

In some embodiments, PDB crystal structure 1FJS were chosen to be used as the initial model of the fXa protein. This structure was imported into an appropriate protein structure visualization program (e.g. the Maestro program), all crystallographic water was deleted, and hydrogens were added to the structure assuming a pH 7 environment. Chain L of the crystal structure was also deleted, since it contained no atoms within 20 Å of the fXa active site. An appropriate molecular mechanics program (e.g. the protein preparation utility found in Maestro) was used to run a restrained minimization of the protein in the presence of the 1FJS crystal structure ligand. This removed bad steric contacts and improved the quality of the protein-protein and protein-ligand hydrogen bonding without large rearrangements of the protein heavy atoms. Using an appropriate molecular mechanics potential energy function (e.g. the OPLSAA-2001 potential), this model of the protein was imported into an appropriate molecular dynamics program (e.g. a modified version of GROMACS containing the velocity version of the Verlet integrator, Andersen temperature controls, and Parrinello-Rahman pressure controls). The system was then solvated in an appropriate molecular mechanics representation of the water solvent (e.g. a cubic TIP4P water box where each boundary was greater than 10 Å away from the protein and added one chlorine ion to neutralize the system).

The energy of the system was minimized to relieve bad steric contacts between the protein and the water and the system was equilibrated for 100 ps with appropriate molecular dynamics protocols (e.g. velocity version of the Verlet integrator and Berendsen temperature and pressure controls at 298 K and 1 bar, where a frame of the system was saved every 1 ps.) The molecular mechanics interactions were modeled with appropriate protocols (e.g. the Lennard-Jones interactions were truncated at 9 Å, the electrostatic interactions were described exactly for pairs within 10 Å and by Particle- Mesh-Ewald for pairs outside of this radius, and all protein heavy atoms were harmonically restrained with spring constants of 1000 kJ/mol/nm). The final 10 ps of equilibration data was used to seed 10 different 1 ns molecular dynamics trajectories with appropriate protocols (e.g. with the velocity version of the Verlet integrator, Andersen temperature controls, and Parrinello-Rahman pressure controls at 298 K and 1 bar). For these simulations the Lennard-Jones, electrostatic forces, and harmonic restraints on the heavy atoms of the protein were the same as in the equilibration simulations. Frames of this simulation were saved every picosecond.

B. Active Site Hydration Analysis of Factor Xa

In order to analyze the thermodynamic and structural properties of the water molecules hydrating the fXa active site, some sensible definition was developed for when a solvating water should be considered within the fXa active site and when it should not. A set of 35 fXa crystal structures with bound inhibitors were used to define the volume of the active site (PDB structures 1EZQ, 1F0R, 1F0S, 1FAX, 1FJS, 1G2L, 1G2M, 1IOE, 1IQE, 1IQF, 1IQG, 1IQH, 1IQI, 1IQJ, 1IQK, 1IQL, 1IQM, 1IQN, 1KSN, 1KYE, 1MQ5, 1MQ6, 1NFU, 1NFW, 1NFX, 1NFY, 1V3X, 1XKA, 1XKB, 2BOK, 2CJI, 2J2U, 2J34, 2J38, 2J4I). A multiple structure alignment was computed between the 35 fXa crystal structures containing inhibitors and the prepared fXa model structure. This alignment rotated the crystal structures onto the prepared fXa structure. This procedure also rotated the inhibitors found in these crystal structures into the active site of the prepared model fXa structure. The results of these alignments were hand inspected for severe steric clashes and none were found. Using this set of aligned structures, the active site was designated as the volume containing all points in space that are within 3 Å of any ligand heavy atom. The position of the active site volume was constant throughout the simulation because the protein heavy atoms were harmonically restrained. The coordinates of all waters observed within this region of space during the 10 ns of simulation data were saved every picosecond. This water distribution was considered to be the equilibrium distribution of water within the fXa active site and its thermodynamic properties were characterized as in the techniques described above.

Several measures of local water structure properties were also calculated for the water molecules found within each hydration site. These were the average number of water neighbors, the average number of hydrogen bonding water neighbors, the fraction of the water neighbors that were hydrogen bonding, and the water exposure of each hydration site. These averages are for all water molecules in each hydration site. The number of neighbors value is the average number of water molecules found within 3.5 Å, where the distance is measured water oxygen to water oxygen. A geometric definition of a hydrogen bond was used where two water molecules were deemed to be hydrogen bonded if their oxygens were within 3.5 Å of each other and at least one oxygen-oxygen-hydrogen angle was less than 30°. The exposure value quantifies to what degree a hydration site is surrounded by other water molecules: a value of unity suggests it is in a water environment similar to the bulk fluid, and a value of zero suggests the hydration site is occluded from any other solvent molecules. The exposure value is computed as the average number of neighbors that water molecules in a hydration site have divided by the average number of neighbors that a water molecule has in the bulk.

C. Construction of the Factor Xa Ligand Binding Affinity Data Sets

Within the PDB, 28 crystal structures of fXa were found bound to various inhibitors with thermodynamic binding data (2BOK, 2J2U, 2BQ7, 1G2L, 2J38, 1G2M, 1KYE, 1F0R, 1F0S, 2BMG, 1NFU, 2J34, 1LQD, 2CJI, 2BQW, 1NFX, 2BOH, 1NFY, 1NFW, 1MQ5, 2J4I, 1EZQ, 1KSN, 1Z6E, 2G00, 1FJS, 2FZZ, 1MQ6). A multiple structure alignment was computed between the 28 fXa crystal structures containing inhibitors and the prepared fXa model structure. This procedure rotated the 28 inhibitors found in these crystal structures into the active site of the prepared model fXa structure. The results of these alignments were hand inspected for severe steric clashes and none were found. The orientations of each of these 28 inhibitors with respect to the prepared model fXa structure were saved and were referred to as the 28 crystal structure ligand set.

From this set of 28 crystal structure ligand set, a set of 31 congeneric inhibitor pairs was prepared. The goal of this set of inhibitor pairs was to isolate the effects of solvent displacement on the free energy of binding. Each congeneric pair was created by either noting that 2 of the crystal structure ligands reported in the prior set were congeneric or by building a congeneric pair from a single crystal structure ligand by deleting or swapping atoms of the crystal structure ligand. Several rules were devised to construct this set. When any two members of the 28 crystal structure ligand set were reported in the same publication and differed by no more than 3 chemical groups, they were considered congeneric pairs. When the publication reporting the crystal structure ligand contained congeneric series data for structurally similar ligands, Three rules were followed to build new congeneric pairs:

1. Atoms were deleted from a crystal structure ligand, and they were not added.
2. Deletions of atoms that resulted in a group that could rotate around a single bond and donate hydrogen bonds were eliminated
3. A congeneric pair that was built by changing the identity of a ligand atom (for instance, by changing a carbon atom to an oxygen atom) can be required to have the change applied to both members of the pair.

These three rules were intended to minimize the error of assuming that the binding mode of the new inhibitor structures, which were built from deleting and swapping atoms of the crystallized inhibitors, would not change. These rules were also intended to minimize differences in contributions to binding affinity from non-solvent related terms for each inhibitor pair, such as the loss of entropy of docking the ligand, the strength of the interaction energy between the ligand and the protein, and the reorganization free energy of the protein. Excluded solvent density effects were expected to dominate this set since these other non-solvent related terms contributing to the free energy of binding would be relatively constant for each congeneric pair. It was also chosen to limit comparison of binding affinities between pairs of ligands that were determined in the same publication, due to the variance in experimental techniques commonly employed. The resulting set can be referred to as the set of 31 congeneric inhibitor pairs.

D. Development and Parameterization of the Displaced-Solvent Functional for Factor Xa A 5-parameter scoring function was devised to determine if the relative binding affinities of the 28 crystal structure ligands and the binding affinity differences of the 31 congeneric inhibitor pairs correlated with the thermodynamic properties of the displaced active site solvent. The form of the functional was a sum over ligand heavy atoms and a sum over hydration sites. Each time a ligand heavy atom was found within some parameterized distance of a hydration site with an interaction energy or excess entropy predicted to be favorable to evacuate by some fit empirical criteria, an additive contribution was summed. The functional itself was $$\Delta G_{lig} = \sum_{lig,hs} E_{rwd}\left(1 - \frac{\vec{r}_{lig} - \vec{r}_{hs}}{R_{co}}\right)\Theta(E_{hs} - E_{co})\Theta(R_{co} - |\vec{r}_{lig} - \vec{r}_{hs}|) - \quad (3)$$

$$T\sum_{lig,hs} S_{rwd}\left(1 - \frac{\vec{r}_{lig} - \vec{r}_{hs}}{R_{co}}\right)\Theta(S^e_{hs} - S_{co})\Theta(R_{co} - |\vec{r}_{lig} - \vec{r}_{hs}|)$$

where $\Delta G_{bind}$ was the predicted binding free energy of the ligand, $R_{co}$ was the distance cutoff for a ligand atom beginning to displace a hydration site, $E_{co}$ was the minimum $E_{hs}$ of a hydration site that was considered energetically depleted, $E_{rwd}$ was the energetic contribution to $AG_{bind}$ for displacing an energetically depleted hydration site, $S_{co}$ was the minimum $S^e$ term of a hydration site that was considered entropically structured, $-TS_{rwd}$ was the Entropic contribution to $\Delta G_{bind}$ for displacing an entropically structured hydration site, and $\Theta$ was the Heaviside step function. A 3-parameter form of this equation was also considered where $R_{co}$=2.8 Å and $-TS_{rwd}$=$E_{rwd}$ were fixed.

The parameters were optimized by a Monte Carlo walk in parameter space. The error-function used to train the parameters was the root-mean-square-deviation of the predicted relative binding free energies of the 28 crystal ligands and the root-mean-square-deviation of the differences in the binding free energies of the 31 congeneric pairs. For the training of the 3- and 5-parameter functionals on the 28 crystal structure ligand set, an initial seed value of $R_{co}$=2.8 Å was chosen, along with $E_{rwd}$=−0.5 kcal/mol, $-TS_{rwd}$=−0.5 kcal/mol, $E_{co}$=−18.5 kcal/mol, and $TS_{co}$=1.5 kcal/mol. Five separate 1000 step optimizations were run where the first move was always accepted and the lowest RMSD value encountered in these optimizations was taken to be the optimal parameter set. The initial seed values used to train the 3- and 5-parameter functionals on the set of 31 congeneric inhibitor pairs were $R_{co}$=2.8 Å, $E_{rwd}$=−1.0 kcal/mol, $-TS_{rwd}$=−1.0 kcal/mol, $E_{co}$=−18.5 kcal/mol, and $TS_{co}$=1.5 kcal/mol. The parameters were then optimized in a procedure similar to that used for the 28 crystal structure ligands.

The error of the resulting optimized functionals were estimated with leave-one-out cross validation. In this technique a functional is trained to an N−1 point subset of data and then the value of point N is predicted with this functional. This is repeated N times, once for each data point, and the error of the functional is estimated by summing the error of the predictions for each of these points. The Pearson correlation coefficient ($R^2$) computed in this procedure for the N data points is bounded between the $R^2$ value found by training of the functional on all N data points and zero. A cross validation $R^2$ value close to the $R^2$ value found by training of the functional on all N data points suggests very little over-fitting has occurred when training the functional.

II. Application to the Test System Cyclin Dependent Kinase 2

A. Structure Preparation and Simulation of Cyclin Dependent Kinase 2

In some embodiments, PDB crystal structure 1 PKD was chosen to be used as the initial model of the CDK2 protein. This structure was imported into an appropriate protein structure visualization program (e.g. the Maestro program), all crystallographic water were deleted, and hydrogens were added to the structure assuming a pH 7 environment. A appropriate molecular mechanics program (e.g. the protein preparation utility found in Maestro) was then used to run a restrained minimization of the protein in the presence of the 1PKD crystal structure ligand. This removed bad steric contacts and improved the quality of the protein-protein and protein-ligand hydrogen bonding without large rearrangements of the protein heavy atoms. Using an appropriate molecular mechanics potential (e.g. the OPLSAA-2001 potential), this model of the protein was imported into an appropriate molecular dynamics program (e.g. a modified version of GROMACS containing the velocity version of the Verlet integrator, Andersen temperature controls, and Parrinello-Rahman pressure controls). The system was then solvated in an appropriate molecular mechanics representation of the water solvent cubic (e.g. a TIP4P water box where each boundary was greater than 10 Å away from the protein).

The energy of the system was minimized to relieve bad steric contacts between the protein and the water and equilibrated 20 replicas of the system for 100 ps with appropriate molecular dynamics protocols (e.g. the Leapfrog integrator and Berendsen temperature and pressure controls at 298 K and 1 bar, where a frame of the system was saved every 1 ps). The molecular mechanics interactions were modeled with appropriate protocols (e.g. the Lennard-Jones interactions were truncated at 9 Å, the electrostatic interactions were described exactly for pairs within 10 Å and by Particle-Mesh-Ewald for pairs outside of this radius, and all protein heavy atoms were harmonically restrained with spring constants of 1000 kJ/mol/nm). This equilibration data was used to seed 20 different 500 ps molecular dynamics trajectories with appropriate protocols (e.g. the Leapfrog integrator under NVE conditions). For these simulations the Lennard-Jones, electrostatic forces, and harmonic restraints on the heavy atoms of the protein were similar to the equilibration simulations. Frames of this simulation were saved every picosecond.

B. Active Site Hydration Analysis of Cyclin Dependent Kinase 2

In order to analyze the thermodynamic and structural properties of the water molecules hydrating the CDK2 active site, some sensible definition was constructed for when a solvating water should be considered within the CDK2 active site and when it should not. A set of 42 CDK2 crystal structures were used with bound inhibitors to define the volume of the active site (PDB structures 1H1P, 1H1S, 1KE5, 1KE6, 1KE7, 1KE8, 1KE9, 1OGU, 1OI9, 1OIQ, 1OIR, 1OIU, 1OIY, 1P2A, 1PXI, 1PXJ, 1PXK, 1PXL, 1PXM, 1PXN, 1PXP, 1VYW, 1VYZ, 1Y8Y, 1Y91, 2B52, 2B53, 2B54, 2BHE, 2BKZ, 2C5P, 2C5V, 2C5X, 2C68, 2C69, 2C6I, 2C6K, 2C6L, 2C6T, 2CLX, 2DUV, and 2FVD). A multiple structure alignment was computed between the CDK2 crystal structures containing inhibitors and the prepared CDK2 model structure merely using residues Glu9-Glu13, Gly17-Ala22, Val30-Ile-36, Leu79-Lys90, Pro131-Asn137, and Leu144-Phe147. The structure alignment used this subset of the protein sequence because the backbone geometry of the protein appeared to be roughly invariant along these portions of the sequence crystal structure to crystal structure. This alignment rotated the crystal structures onto the prepared CDK2 structure, which also rotated the inhibitors found in these crystal structures into the active site of the prepared model CDK2 structure. The results of these alignments were hand inspected for severe steric clashes and none were found. Using this set of aligned structures, the active site was designated as the volume containing all points in space that are within 3 Å of any ligand heavy atom. The position of the active site volume was constant throughout the simulation because the protein heavy atoms were harmonically restrained. The coordinates of all waters observed within this region of space during the 10 ns of simulation data were saved every picosecond. This water distribution was considered to be the equilibrium distribution water within the CDK2 active site and its thermodynamic properties were characterized according to the techniques described in the detailed description. Several measures of local water structure properties were also calculated for the water molecules found within each hydration site, as was done for CDK2.

C. Construction of the Cyclin Dependent Kinase 2 Ligand Binding Affinity Data Sets From the set of CDK2 crystal structures aligned with the model 1PKD structure, a set of 47 congeneric inhibitor pairs was prepared. The goal of this set of inhibitor pairs was to isolate the effects of solvent displacement on the free energy of binding. Each congeneric pair was created by either noting that 2 of the crystal structure ligands reported in the prior set were congeneric or by building a congeneric pair from a single crystal structure ligand by deleting or swapping atoms of the crystal structure ligand. Several rules were devised to construct this set. When any two members of the CDK2 crystal structure ligand set were reported in the same publication, differed by no more than 3 chemical groups, and merely differed by deletions of atoms; they then were considered congeneric pairs. When the publication reporting the crystal structure ligand contained congeneric series data for structurally similar ligands, three rules were followed to build new congeneric pairs:

1. Atoms were deleted from a crystal structure ligand, and they were not added.
2. Deletions of atoms that resulted in a group that could rotate around a single bond and donate hydrogen bonds were eliminated
3. A congeneric pair that was built by changing the identity of a ligand atom (for instance, by changing a carbon atom to an oxygen atom) can be required to have the change applied to both members of the pair.

These three rules were intended to minimize the error of assuming that the binding mode of the new inhibitor structures, which were built from deleting and swapping atoms of the crystallized inhibitors, would not change. These rules were also intended to minimize differences in contributions to binding affinity from non-solvent related terms for each inhibitor pair, such as the loss of entropy of docking the ligand, the strength of the interaction energy between the ligand and the protein, and the reorganization free energy of the protein. Excluded solvent density effects were expected to dominate this set since these other non-solvent related terms contributing to the free energy of binding would be relatively constant for each congeneric pair. It was chosen to compare binding affinities between pairs of ligands that were determined in the same publication and in complex with either Cyclin A or Cyclin E, due to the variance in experimental techniques commonly employed. The resulting set was designated as the set of 47 CDK2 congeneric inhibitor pairs.

D. Development and Parameterization of the Displaced-Solvent Functional for Cyclin Dependent Kinase 2

The 5 parameter and 3 parameter forms of the displaced solvent functional were trained to the set of 47 congeneric inhibitor pairs of CDK2 through techniques similar to those used to train the functionals for fXa. The functional was also trained to a combined set of 31 congeneric inhibitor pairs of fXa and 47 congeneric inhibitor pairs of CDK2. The error in these parameter fittings were also estimated with leave-one-out cross validation.

III. Results

Figure 2:
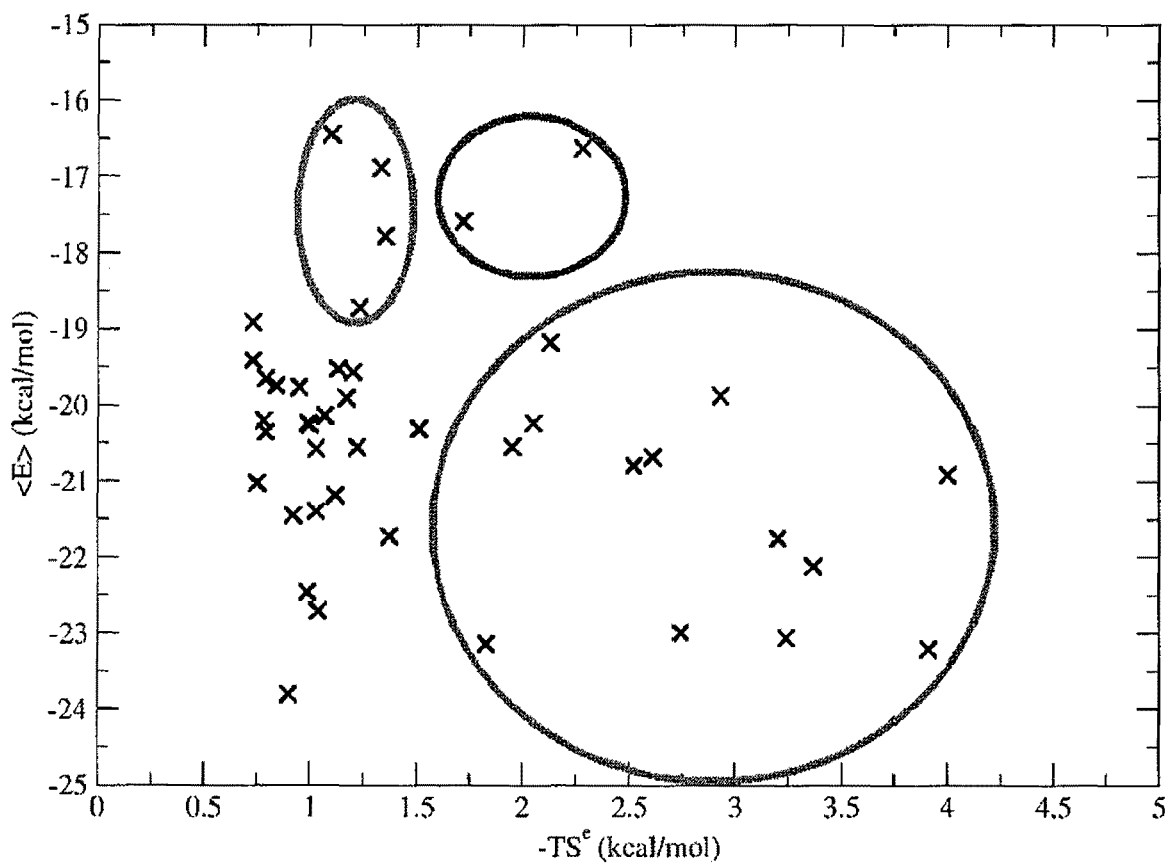
FIG. 2 is a depiction according to some embodiments of the described subject matter. Those hydration sites expected to contribute favorably to binding when evacuated by the ligand are here shown within the factor Xa active site in wire frame. Those expected to contribute energetically are shown in gray, those expected to contribute entropically are shown in green, and those expected to contribute energetically and entropically are shown in purple. The S1 and S4 pockets are labeled in yellow, as are several hydration sites discussed in the text.

A. Mapping of the Thermodynamic Properties of the Active Site Solvent of Factor Xa The data for each fXa hydration site is presented in Table 1. FIG. 1 shows the calculated energies and excess entropies for each of the hydration sites in the fXa binding cavity. Relative to other hydration sites, the hydration sites circled in gray had poor system interaction energies, the hydration sites circled in green had unfavorable excess entropies, and the hydration sites circled in purple had both relatively poor system interaction energies and entropies. FIG. 2 shows the resulting 3-dimensional active site hydration map with this same color coding.

The hydration site map generated by the described subject matter for the test system fXa depicted in FIG. 2 elucidated several features of the experimentally known SAR of the fXa ligands. Factor Xa inhibitors generally bind in an L-shaped conformation, where one group of the ligand occupies the anionic S1 pocket lined by residues Asp189, Ser195, and Tyr228 and another group of the ligand occupies the aromatic S4 pocket lined by residues Tyr99, Phe174, and Trp215. Typically, a fairly rigid linker group will bridge these two interaction sites. The solvent analysis identified three enthalpically unfavorable hydration sites, i.e., sites 13, 18, and 21, solvating the fXa S4 pocket. This finding agreed with the experimental result that the S4 pocket has an exceptionally high affinity for hydrophobic groups. A high excess chemical potential hydration site was identified, site 12, solvating Tyr228 in the S1 pocket. Several research groups have found that introducing a ligand chlorine atom at this location, and hence displacing the water from this site, makes a large favorable contribution to the binding affinity. Additionally, an energetically depleted hydration site was identified, site 17, solvating the disulfide bridge between Cys191 and Cys220. Displacement of water from this site was expected to make favorable contributions to the binding free energy. This agrees with several reported chemical series targeting this site.

This hydration map was compared with the locations of active site crystallographic waters from the fXa apo-structure, crystal structure 1HCG. Of the 11 crystallographic waters that resolve within the fXa active site, 9 of these crystallographic waters are within 1.5 Å of a hydration site, and all of the crystallographic waters are within 2.5 Å of a hydration site. More hydration sites were identified in the active site than crystallographically resolved waters. However, this discrepancy is expected since the 1HCG crystal structure was merely solved to a resolution of 2.2 Å, and it has been noted that the number of crystallographic water molecules identified in X-ray crystallography of proteins is quite sensitive to resolution (an average of 1.0 crystal waters per protein residue is expected at a resolution of 2 Å, but an average of 1.6-1.7 crystal waters per residue is expected at a resolution of 1 Å). The number and location of crystallographic waters identified in X-ray crystallography of proteins has also been found to be sensitive to temperature, pH, solvent conditions, and the crystal packing configuration. Given these sources of noise, the agreement was found to be satisfactory and in line with other similar comparisons of the solvent distributions obtained from molecular dynamics simulations with those obtained from X-ray crystallography.

Figure 3:
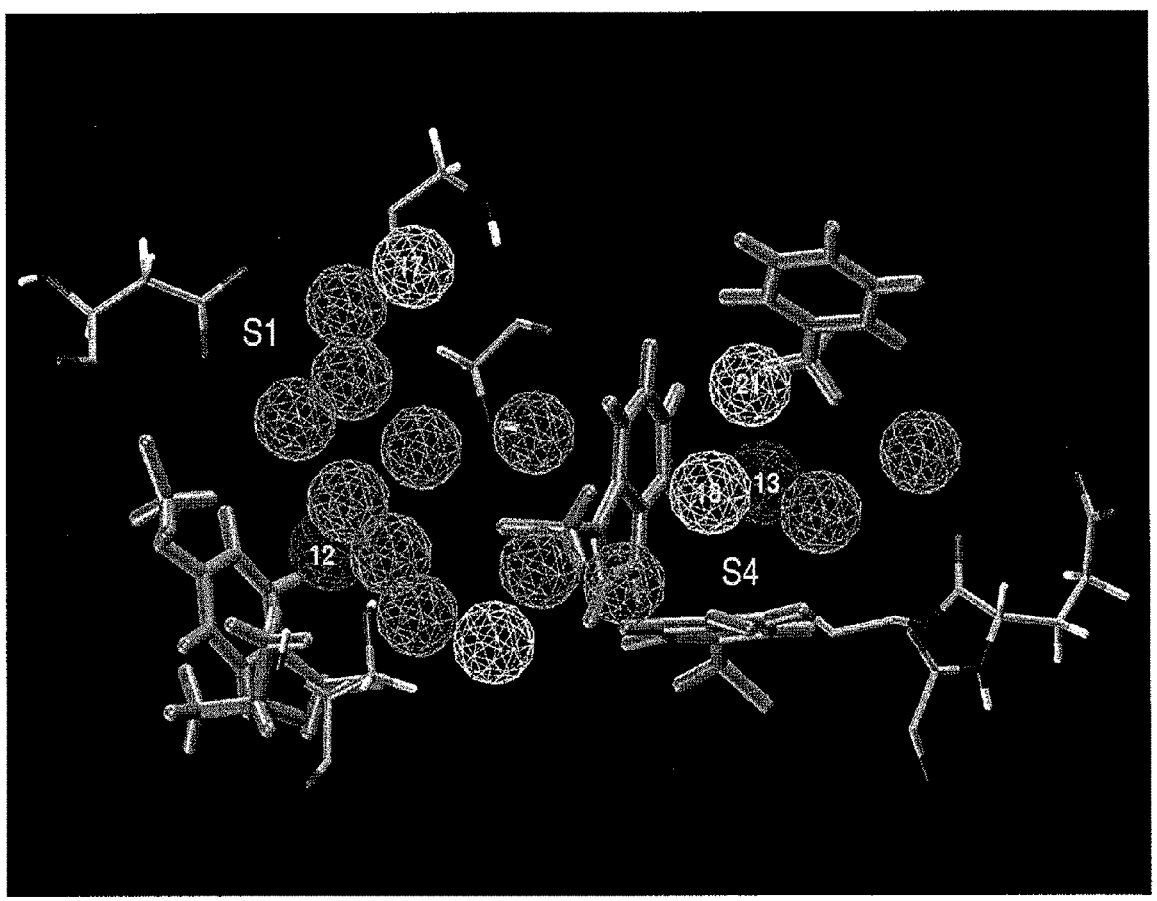
FIG. 3 is a depiction according to some embodiments of the described subject matter. The depiction concerns computed relative activities using the 5-parameter form of equation 2 versus experimental relative activities of the 31 congeneric inhibitor pairs with factor Xa. Note the stability of this fit under leave-one-out cross validation.
Figure 4:
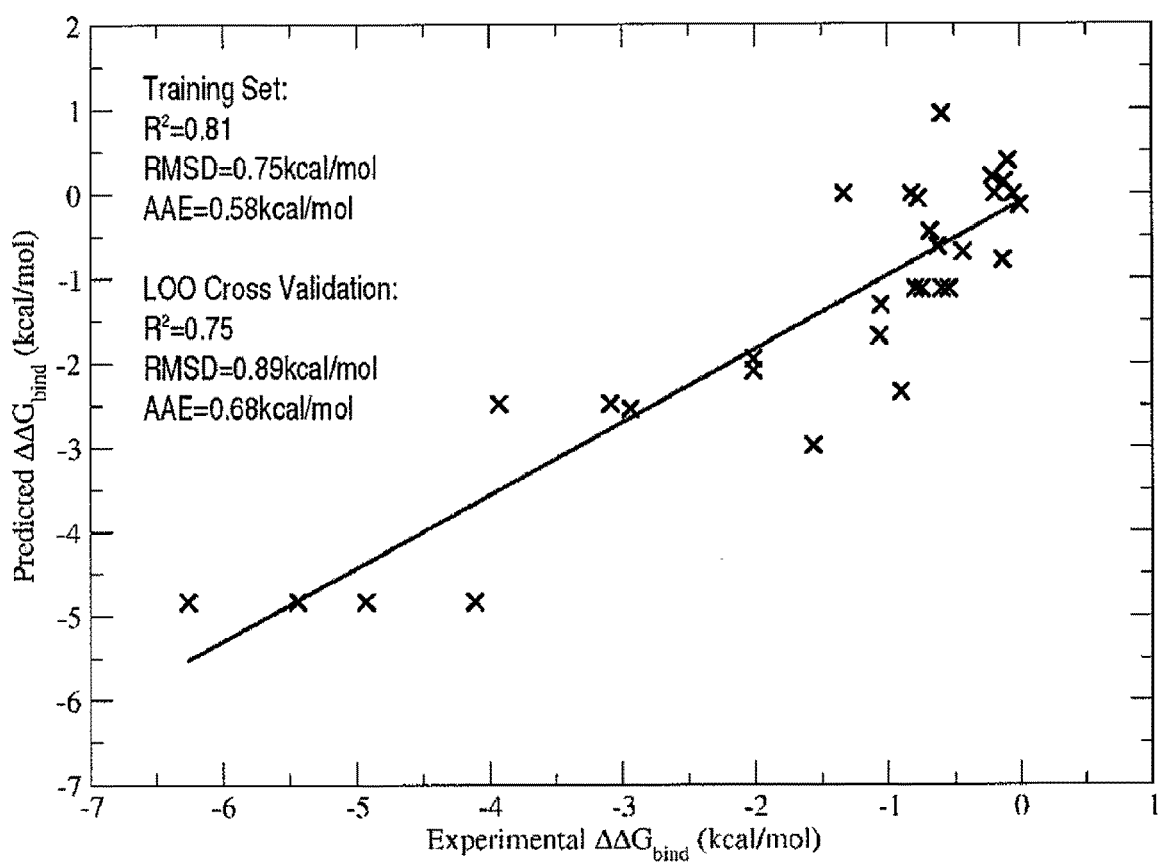
FIG. 4 is a depiction according to some embodiments of the described subject matter. The depiction concerns computed relative activities using the 3-parameter form of equation 2 versus experimental relative activities of the 31 congeneric inhibitor pairs with factor Xa. Note the stability of this fit under leave-one-out cross validation.

B. Development and Testing of the Displaced-Solvent Functional on the Set of the Factor Xa Congeneric Inhibitor Pairs A dataset of 31 congeneric inhibitor pairs of fXa (see section I.C) (Table 2) was prepared. These 31 congeneric inhibitor pairs were pairs of fXa ligands that differed by at most three chemical groups. It was expected that excluded solvent density effects would dominate this dataset since the other terms—the protein reorganization free energy, ligand conformational entropy, etc.—would be largely a consequence of the ligand scaffold shared by both members of the pair. The parameters of the displaced-solvent functionals were optimized to reproduce the experimentally measured differences in binding affinity between each of these congeneric ligand pairs. The error of the resulting functionals were estimated with leave-one-out cross validation. The resulting values of the parameters can be found in Table 3 and plots of the predicted differences in binding free energy versus the experimental values are shown in FIGS. 3 and 4. The agreement of the predictions of the functionals with the experimental data was notable: the Pearson correlation coefficient ($R^2$) was 0.81 for both the 3-parameter and 5-parameter functionals. Under leave-one-out cross-validation, the $R^2$ value degraded to 0.80 and 0.75, respectively. From the good numerical agreement observed over the 6 kcal/mol free energy range of modifications plotted in FIGS. 3 and 4, this technique was well differentiated from modifications that make large contributions to the binding affinity from modifications that merely make small modifications to the binding affinity for this fXa test system. The predictive ability of the displaced solvent functional on this series confirms that the effect on the binding free energy of small complementary chemical modifications to existing leads can largely be understood by an analysis of the molecular properties of the solvent alone. Several congeneric ligand pairs were instructive in clarifying the particular strengths of this approach.

Figure 5:
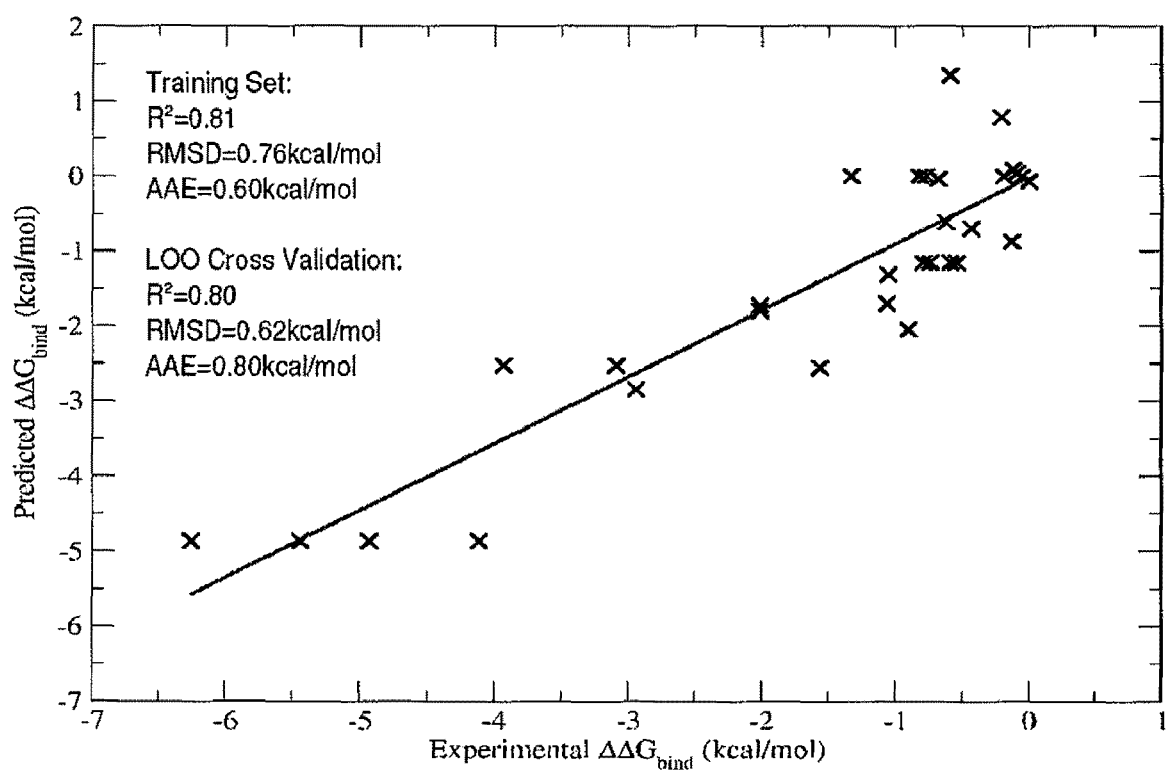
FIG. 5 is a depiction according to some embodiments of the described subject matter. The depiction concerns ligand 2J4I:38 (left) and ligand 2J4I:GSJ (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-6.26$ kcal/mol. The optimized 3- and 5-parameter functionals predicted $\Delta\Delta G_{3p}=-4.87$ and $\Delta\Delta G_{5p}=-4.83$ respectively. The isopropyl group of ligand 2J4I:GSJ displaces three energetically depleted hydration sites, two of which are predicted to also be entropically structured, which resulted in a large predicted contribution to the binding affinity of the complex.

Congeneric ligands 2J4I:38 and 2J4I:GSJ, depicted in FIG. 5, were representative of the types of modifications that would contribute well to the binding affinity. These ligands differ in that GSJ has an additional isopropyl group located in the S4 pocket. This isopropyl group fills a portion of the S4 pocket that is lined by the side chains of residues Tyr99, Phe174, and Trp215 and, in the absence of the ligand, is principally solvated by hydration sites 13, 18, and 21. Hydration site 13 is in close contact (<4.5 Å) with each of these three aromatic side chains and has a very low exposure parameter of 0.53. Water molecules in this hydration site cannot form hydrogen bonds with the hydrophobic protein and maintain an average of 2.05 water-water hydrogen bonds, which leads to relatively unfavorable system interaction energies. The hydrogen bonds that it does form are mainly donated by hydration sites 18 and 21 and very rarely by hydration site 1. The orientational and translational restrictions necessary to maintain this hydrogen bonding profile result in relatively unfavorable excess entropies for water at this hydration site. The hydrophobic enclosure for hydration sites 18 and 21 is not as tight (exposure parameters of 0.66 and 0.74, respectively); however, the environment is otherwise qualitatively similar. Both these hydration sites have above-average system interaction energies due to the hydrophobic bulk of the protein enclosing them, and hydration site 18 was also identified by the empirical criteria of the described subject matter to be entropically unfavorable, although it was a borderline case. GSJ's additional isopropyl group expels water from all three of the above-described hydration sites: hydration sites 13 and 18 were predicted by the optimized displaced-solvent functionals to make both energetic and entropic contributions to binding, and hydration site 21 was predicted to merely make energetic contributions. The experimentally measured affinity difference between these two compounds is $\Delta\Delta G_{exp}=-6.26$ kcal/mol. The optimized 3- and 5-parameter functionals predicted $\Delta\Delta G_{3p}=-4.87$ and $\Delta\Delta G_{5p}=-4.83$, respectively. This agreed with the experimental finding that adding an isopropyl group to ligand 2J4I:38 at this location makes a large and favorable contribution to the binding free energy. The congeneric ligand pair 2J4I:32/2J4I:33 ($\Delta\Delta G_{exp}=-4.11$ kcal/mol) has precisely the same hydrogen/isopropyl substitution as the 2J4I:38/2J4I:GSJ pair, and therefore the same values for $\Delta\Delta G_{3p}$ and $\Delta\Delta G_{5p}$ of −4.87 and −4.83 kcal/mol, respectively, which matches very well with $\Delta\Delta G_{exp}$.

Figure 6:
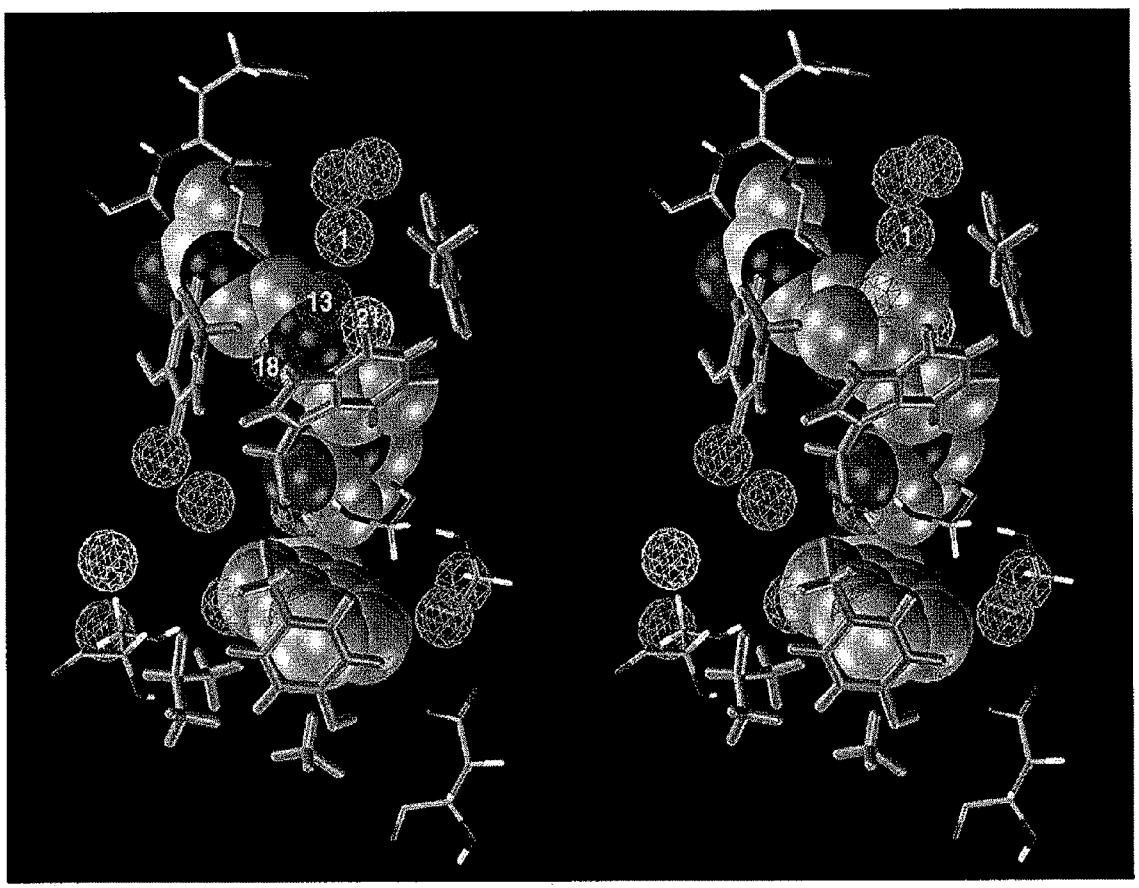
FIG. 6 is a depiction according to some embodiments of the described subject matter. The depiction concerns ligand 1MQ5:XLC (left) and ligand 1MQ6:XLD (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-2.94$ kcal/mol. The optimized 3- and 5-parameter functionals predicted $\Delta\Delta G_{3p}=-2.85$ and $\Delta\Delta G_{5p}=-2.54$ respectively. Unlike the S4 group of ligand 1MQ5:XLC, the S4 pocket group of ligand 1MQ6:XLD displaced the energetically depleted and entropically structured hydration site 13 and partially displaced entropically structured hydration sites 20, which resulted in a large solvent related contribution to the binding affinity quantitatively predicted.

The congeneric ligands 1MQ5:XLC and 1MQ6:XLD are depicted in FIG. 6. This pair has a more subtle modification of the group binding the S4 pocket than the 2J4I:38-2J4I:GSJ congeneric pair described above. For this pair, the S4 binding group found in ligand 1MQ6:XLD overlapped with hydration sites 13 and 20, whereas the S4 binding group of ligand 1MQ5:XLC did not. As noted above, expulsion of water from hydration site 13 is expected to make both favorable energetic and entropic contributions to binding. Water in hydration site 20 has favorable energetic interactions due to several well-formed hydrogen bonds: water molecules occupying this site predominately donate a hydrogen bond to the backbone carbonyl group of Glu97, nearly always receive a hydrogen bond from hydration site 4, and have good hydrogen bonding interactions with hydration site 35. Hydration site 20, though, also incurred unfavorable contributions to its excess entropy due to the structuring required to maintain these favorable interactions. When displaced by the S4 binding group of ligand 1MQ6:XLD, an electropositive carbon (the carbon is bound to an oxygen) comes into close contact with the backbone carbonyl group of Glu97. This electropositive carbon likely recaptures much of the interaction energy between the protein carbonyl group and the water in hydration site 20 without the associated entropic cost. From these water thermodynamics considerations, the optimized 3- and 5-parameter displaced-solvent functionals predict affinity differences of $\Delta\Delta G_{3p}=-2.85$ and $\Delta\Delta G_{5p}=-2.54$, respectively. The experimental difference binding affinity between the two ligands is $\Delta\Delta G_{exp}=-2.94$ kcal/mol.

Figure 7:
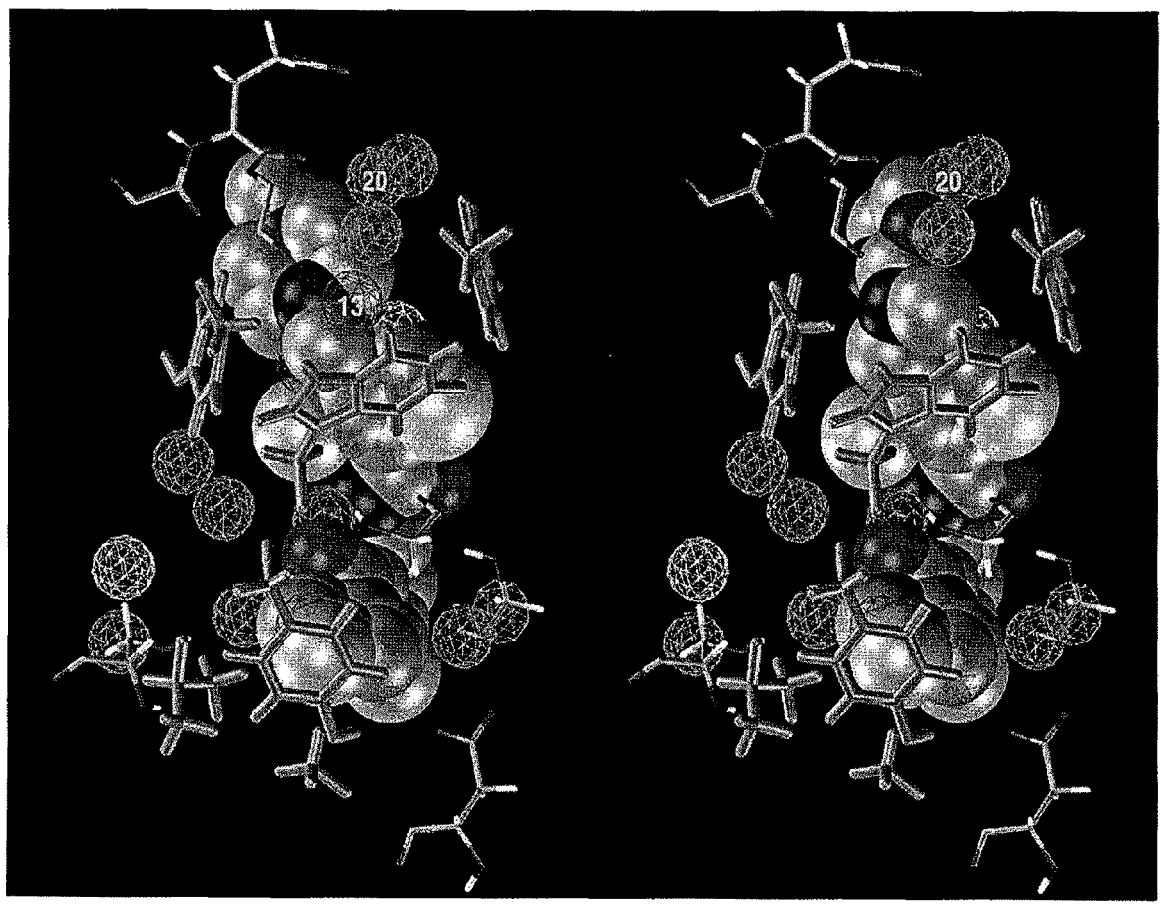
FIG. 7 is a depiction according to some embodiments of the described subject matter. The depiction concerns ligand 2BQ7:IID (left) and ligand 2BQW:IIE (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-2.01$ kcal/mol. The optimized 3- and 5-parameter functionals predicted $\Delta\Delta G_{3p}=-1.73$ and $\Delta\Delta G_{5p}=-1.95$ respectively. Unlike the S1 group of ligand 2BQ7:IID, the S1 pocket group of ligand 2BQW:IIE displaces the energetically depleted and entropically structured hydration site 12 found within the S1 subgroove. The contribution to the binding affinity predicted by the 3-parameter and 5-parameter displaced-solvent functionals agreed with experiments.

The congeneric ligands 2BQ7:IID and 2BQW:IIE are depicted in FIG. 7. This congeneric pair isolates the contribution of inserting a ligand chlorine atom into the region of the S1 pocket lined by the side chains of residues Ala190, Val213, and Tyr228. The chlorine atom on 2BQW:IIE displaces water from hydration site 12, which is tightly enclosed by the side chains of residues Ala190, Val213, and Tyr228. The exposure parameter of this hydration site is merely 0.32. This tight enclosure by hydrophobic groups caused the system interaction energy of water in this hydration site to be several kcal/mol less favorable than in the neat fluid. Water molecules in this site maintained hydrogen bonds with its few water neighbors 92% of the simulation time, which made unfavorable contributions to its excess entropy. The location of this hydration site coincided with the location of a structurally conserved water molecule that several studies have shown is favorable to displace. The experimentally measured affinity difference between these two compounds is $\Delta\Delta G_{exp}=-2.01$ kcal/mol, whereas the optimized 3- and 5-parameter functionals predicted are $\Delta\Delta G_{3p}=-1.73$ and $\Delta\Delta G_{5p}=-1.95$, respectively.

Figure 8:
FIG. 8 is a depiction according to some embodiments of the described subject matter. The depiction concerns ligand 2BMG:25 (left) and ligand 2BMG:I1H (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-1.05$ kcal/mol. The optimized 3- and 5-parameter functionals predicted $\Delta\Delta G_{3p}=-1.31$ and $\Delta\Delta G_{5p}=-1.31$ respectively. The addition of a methoxyl group to ligand 2BMG:I1H displaces an energetically depleted hydration site from the linker region of the active site which solvates a disulfide bond between residues 191 and 220. Both functionals predicted the contribution of displacing this hydration site to the binding affinity of the complex with high accuracy.

The congeneric ligands 2BMG:25 and 2BMG:I1H are depicted in FIG. 8. These ligands differ in that ligand 2BMG:I1H has an additional methoxy group that displaced water from hydration site 17, which solvates a disulfide bond between Cys191 and Cys220. Predicting the favorability of adding a methoxy group at this position is highly nontrivial. The portion of the active site solvated by hydration site 17 did not appear especially hydrophobic (the side chains of Gln192 and Arg144 and the backbone carbonyl group of Glu147 are within 4 Å of its position); however, due to the concave topography (exposure parameter of 0.48) of the protein surface, water molecules in this hydration site are unable to form as energetically favorable hydrogen bonding interactions with the protein as they would with water in the bulk. This resulted in the system interaction energy of hydration site 17 to be ~3 kcal/mol less favorable than water molecules in the bulk fluid. The size scale of individual water molecules is important here, since a field of infinitesimal dipoles would easily solvate both polar side chains and the surrounding dipolar fluid. The two displaced-solvent functionals each predict the difference in the binding affinity of ligands 2BMG:25 and 2BMG:I1H within 0.26 kcal/mol of the experimentally measured value.

Figure 9:
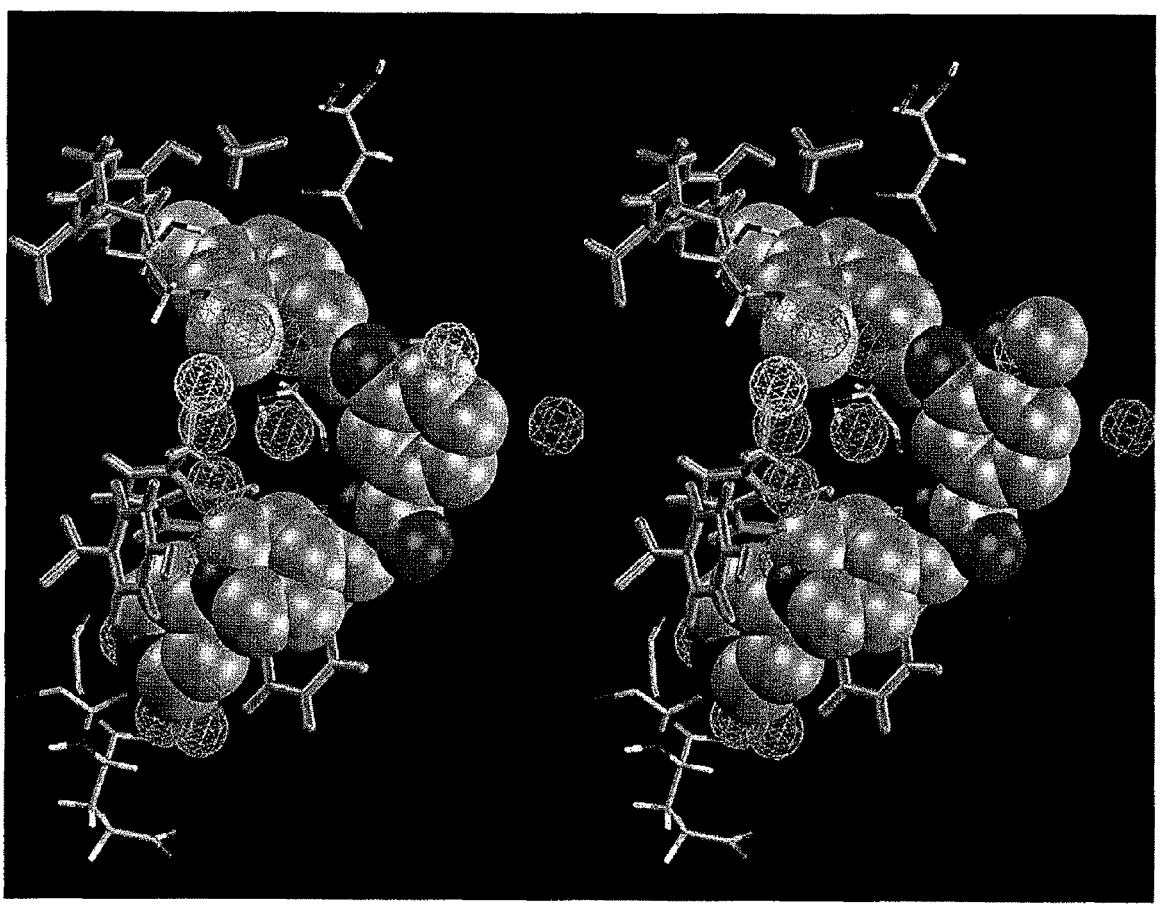
FIG. 9 is a depiction according to some embodiments of the described subject matter. The depiction concerns ligand 1V3X:D76 (left) and ligand 1V3X:57 (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-0.05$ kcal/mol. The optimized 3- and 5-parameter functionals predicted $\Delta\Delta G_{3p}=0.0$ and $\Delta\Delta G_5=0.0$ respectively. The addition of the amide group to ligand D76 contribute negligibly to the binding affinity of the complex, which the technique predicted from the location of the amide group away from any structured or energetically depleted hydration sites.

The congeneric ligands 1V3X:D76 and 1V3X:57 are depicted in FIG. 9. Ligand 1V3X:57 has an additional amide group which is oriented away from the protein in the linker region of the complex. The displaced-solvent functionals correctly predicted that the addition of this group has a marginal contribution to the binding affinity. This is because the amide group does not displace water from any contributing hydration site. It is interesting to note that the size of this added group is approximately equal to that of the isopropyl group added in ligand pair 2J4I:38-2J4I:GSJ. This underscored that the displaced-solvent functional evaluated a weighted shape complementarity—i.e., it rewarded the introduction of complementary groups where predicted to make large contributions from the solvent properties and does not reward shape complementarity away from these regions. The experimentally measured affinity difference between these two compounds is $\Delta\Delta G_{exp}=-0.05$ kcal/mol. The optimized 3- and 5-parameter functionals both predict no affinity difference between the two compounds, consistent with the experimental $\Delta\Delta G$.

Figure 10:
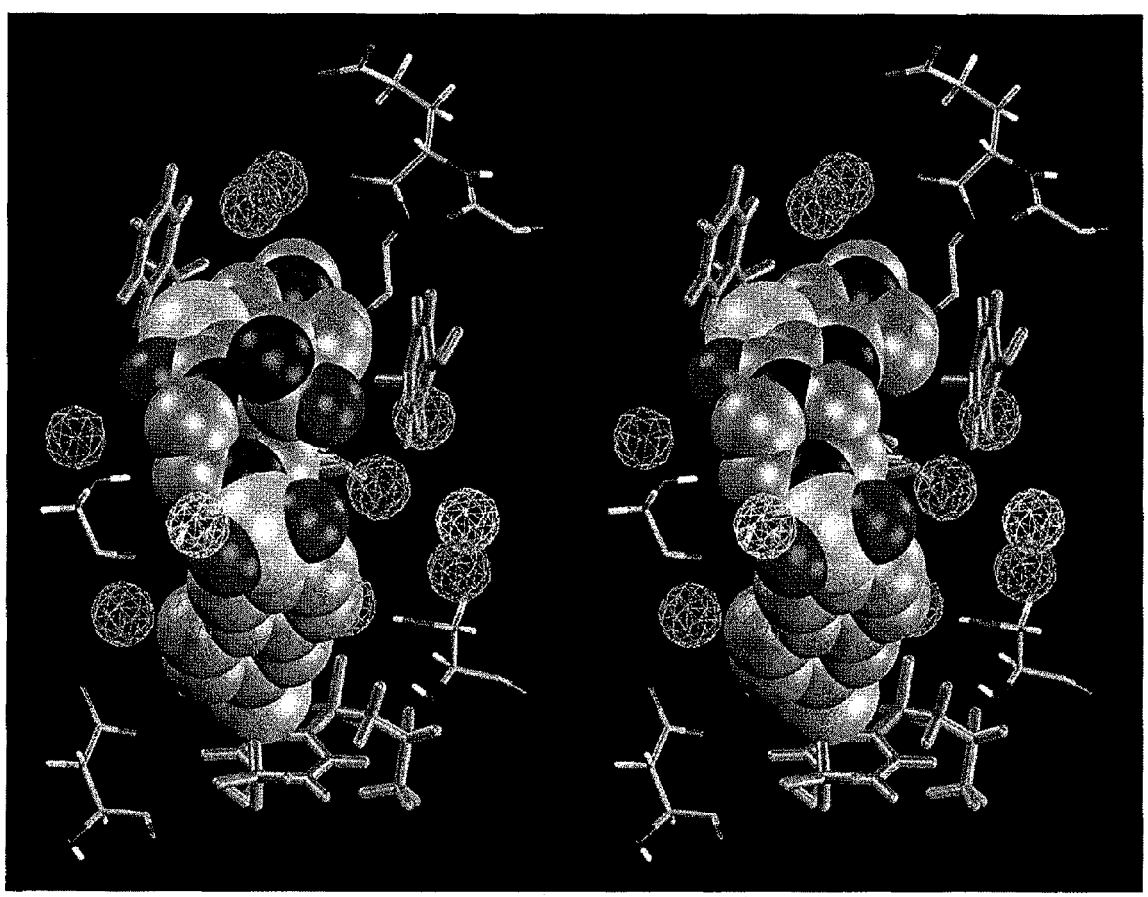
FIG. 10 is a depiction according to some embodiments of the described subject matter. The depiction concerns ligand 1NFX:RDR (left) and ligand 1NFU:RRR (right) in the factor Xa active site. The hydration sites that receive an energetic score in equation 2 are depicted in gray wire frame, the hydration sites that receive an entropic score are depicted in green wire frame, and the hydration sites that receive both energetic and entropic scores are depicted in purple wire frame. Several hydration sites discussed in the text are labeled in yellow. The experimentally measured affinity difference between these two compounds is $\Delta\Delta G_{exp}=-0.59$ kcal/mol. The optimized 3- and 5-parameter functionals predicted $\Delta\Delta G_{3p}=+1.94$ and $\Delta\Delta G_{5p}=+1.53$ respectively. The poor agreement of the theory with experiment here is due to the poor interaction energy of the S1 pocket sulfur atom of 1NFX:RDR with Ser195 compared with hydration 5, which is not displaced when ligand 1NFU:RRR docks with the receptor.

Congeneric ligands 1NFX:RDR and 1NFW:RRR are depicted in FIG. 10. These ligands differ by a substantial modification to the ring that binds the S1 pocket. They also differ by the removal of an ethanol group that is distant from any contributing hydration sites. The S1 binding group of ligand 1NFX:RDR has a sulfur atom in close contact with Ser195. This sulfur atom displaces water from hydration site 5, whereas ligand 1NFW:RRR does not displace water from this site. Water molecules in this hydration site have favorable interactions with the protein and the surrounding waters but are entropically structured. The structuring and corresponding entropic penalties come from the large degree of enclosure (exposure parameter of 0.5) in combination with the energetic demands of maintaining favorable hydrogen bonding interactions with the protein and surrounding water; notably, a persistent hydrogen bond is donated from Ser195 to the water molecules in this site. The displacement of water leads the optimized 3- and 5-parameter functionals to predict $\Delta\Delta G_{3p}=+1.94$ and $\Delta\Delta G_{5p}=+1.53$, respectively. However, the experimentally measured difference in binding affinities is $\Delta G_{exp}=-0.59$ kcal/mol. The scoring function performed less desirably for this inhibitor pair because the sulfur atom in the benzothiophene group of ligand 1NFX:RDR and Ser195 questioned that the added chemical groups must be complementary to the protein surface. Thus, though the displacement of water from hydration site 5 should contribute favorably to the binding free energy, it is more than offset by the loss of hydrogen bonding energy between the water and Ser195. This resulted in the displaced-solvent functional predicting 1NFX:RDR would be the tighter binding ligand, in disagreement with the experimental data.

Figure 11:
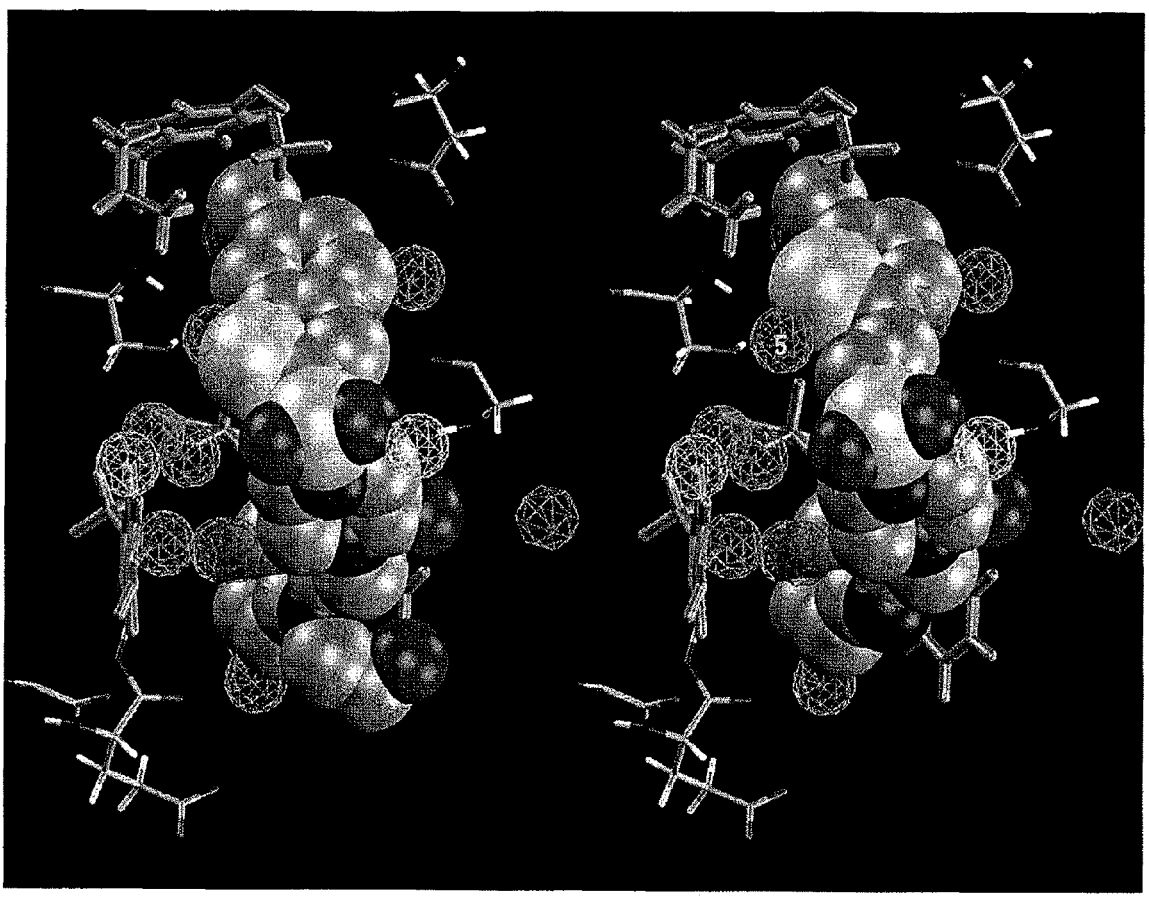
FIG. 11 is a depiction according to some embodiments of the described subject matter. The depiction concerns computed activities using the 5-parameter form of equation 2 versus experimental activities for the set of 28 inhibitors with factor Xa. The poor stability of the fit under cross validation suggested substantial over-fitting.
Figure 12:
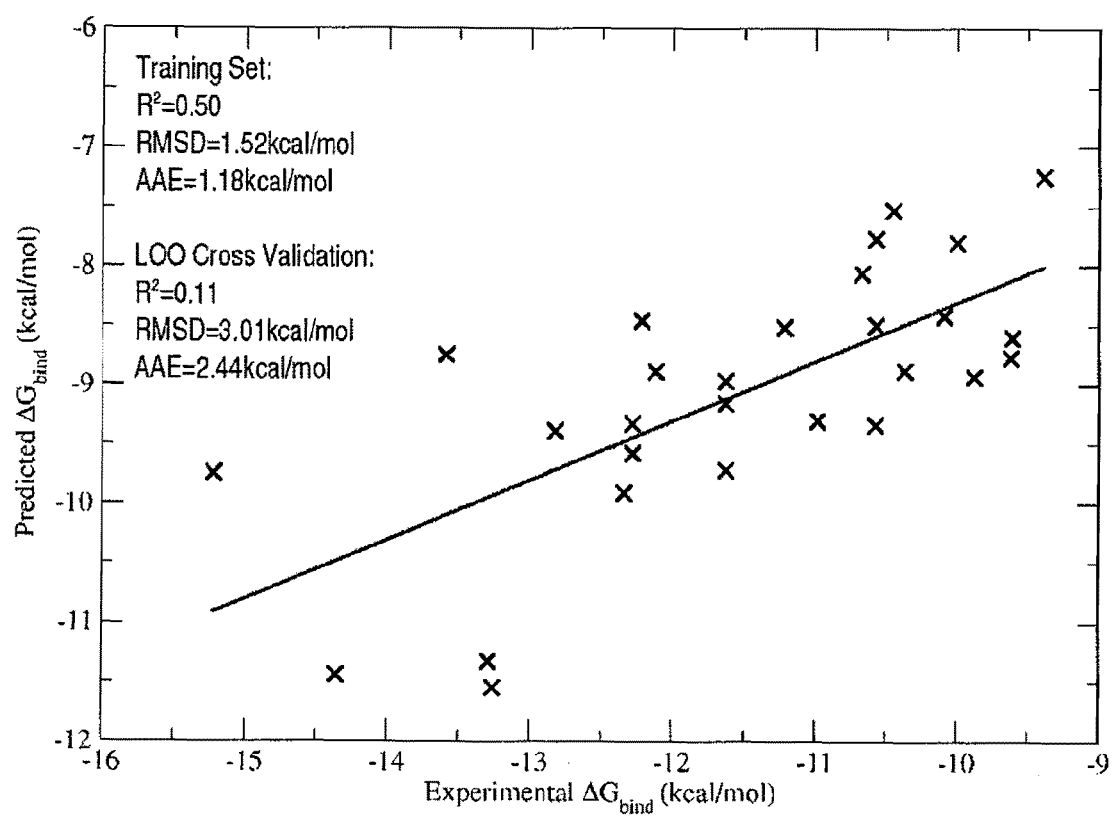
FIG. 12 is a depiction according to some embodiments of the described subject matter. The depiction concerns computed activities using the 5-parameter form of equation 2 versus experimental activities for the set of 28 inhibitors with factor Xa. The moderate stability of the fit under cross validation suggested the problems associated with over-fitting were reduced when the three parameter form of equation 2 was used.

C. Development and Testing of the Displaced-Solvent Functional on the Set of 28 Factor Xa Crystal Structure Ligands In addition to the set of 31 congeneric pairs, a dataset of 28 inhibitors was prepared taken from solved fXa crystal structures (see subsection C) (Table 4). These fXa ligands belonged to many different congeneric series, and typically did not share a common chemical scaffold with each other. In the previous section it was hypothesized the contributions to the free energy of binding from changes in conformational entropy, protein-ligand interaction energy, and protein reorganization free energy would be similar for ligand pairs that shared a common chemical scaffold. If this was the case, the differences in the binding free energies of congeneric pairs could be understood mainly by an analysis of the displaced solvent alone. The success of the 3- and 5-parameter displaced-solvent functional outlined in the previous section supports the validity of this hypothesis. However, for ligand pairs that do not share a common scaffold, it would be expected that differences in these contributions would not be small and that predictions based solely on an analysis of the solvent would be less successful. Despite this concern, since the functional performed well over the set of congeneric pair, it was desirable to determine how much of the binding affinities of these ligands could be understood from merely the contributions described by the displaced-solvent functional, as measured by the RMSD, absolute average error, and $R^2$ values. To study this question, the 3- and 5-parameter displaced-solvent functionals were optimized to reproduce the experimentally measured differences in binding affinities between 378 unique ligand pairs (all combinations) of this 28 ligand set, and leave-one-out (LOO) cross validation was performed to better estimate the error of the functionals. Values of the parameters can be found in Table 5 and the agreement of the fit functionals with the experimental data can be found in FIGS. 11 and 12. Although the 3- and 5-parameter functionals could be tuned to correlate reasonably well with the experimental data ($R^2$ of 0.50 and 0.48, respectively), the performance under leave-one-out cross validation suggested substantial over-fitting of the 5-parameter functional (LOO $R^2=0.11$). Notably, though, the cross validated $R^2$ of 0.30 for the 3-parameter fit indicated terms of the type described by the displaced-solvent functional are important to understanding the absolute binding thermodynamics of fXa ligand, but also clearly indicated that more traditional terms can also be helpful to quantitatively predict absolute binding free energies with desired accuracies.

In both the 3- and 5-parameter fits of the displaced-solvent functional to the set of 28 crystal structure ligands, two particular ligands, 1MQ6:XLD and 1FJS:Z34, were consistently the worst outliers in the set. Both of these ligands have excellent overlap with contributing hydration sites, but were outscored by ligands that placed larger aromatic groups at similar positions in the binding pocket, such as ligands 1Z6E:IK8, 2FZZ:4QC, and 2G00:5QC. This error was expected because the pair-wise reward of atoms in close contact with the hydration sites approximated to what degree the contributing hydration sites were displaced by the surface of the ligand. Thus, when an aromatic group displaced a hydration site, a disproportionately large number of ligand atoms contributed in the displaced-solvent functional since the tighter covalent bonding in these groups placed many ligand atoms closer in space to the hydration site than could be seen otherwise. When ligands 1MQ6:XLD and 1FJS:Z34 were excluded from the fit, the leave-one-out cross validation of the 3- and 5-parameter functionals yielded $R^2$ values of 0.40 and 0.55, respectively. This dramatic improvement of the stability and quality of the fit underscores how poor the linear pair-wise approximation of the excluded volume of the ligand was for inhibitors 1MQ6:XLD and 1FJS:Z34. It is also possible that the known favorable electrostatic interaction between 1FJS:Z34 and the fXa S4 pocket, which was not described by the displaced-solvent functional, contributed to 1FJS:Z34 being an outlier in this data set.

D. Cross Testing of the Trained Displaced Solvent Density Functionals for Factor Xa The transferability of the parameters trained on the set of 31 congeneric inhibitor pairs to the set of 28 crystal structure ligands (Table 6) was determined. The optimized 3- and 5-parameter functionals trained on the set of 31 congeneric inhibitor pairs each had $R^2$ values of 0.17 when predicting the relative binding affinities of the 28 crystal structure ligands to fXa. The functionals performed poorly because the values of the parameters obtained from training to the set of congeneric pairs typically predicted the difference in binding affinity between crystal structure pairs to be much too large (often greater than 10 kcal/mol). The reason for this can be subtle: typically it can be that the tightest binding compound of a series will be crystallized, and even then it can be typically crystallized if it binds with a submicromolar affinity. Thus, if a ligand displaces a sub-optimal portion of the active site solvent density, then it, by construction, can become a crystallized ligand if it is possible to tune the other contributions to the free energy (ligand entropy, ligand desolvation free energy, protein ligand interaction energy, etc.) to offset this suboptimal active-site-solvent evacuation, resulting in the needed submicromolar affinity. So the magnitude of the contributions predicted by the displaced-solvent functionals can be qualitatively correct, but the other terms not described by the functional systematically offset them.

A contrast to this result was found when the 3- and 5-parameter functionals trained on the set of 28 crystal structure ligands were used to predict the binding affinity differences of the set of 31 congeneric inhibitor pairs. The 3- and 5-parameter functionals trained on a set of crystal structure ligands predicted the binding affinity differences of the set of 31 congeneric inhibitor pairs with $R^2$ values of 0.53 and 0.59, respectively. This result suggested the functional form of the displaced-solvent functional can have fundamental features that lend themselves to ranking the binding affinities of compounds that differ by deletions of atoms—i.e., as long as the chosen parameters are physically reasonable, the performance of the functional over congeneric sets of this kind can be quite good.

E. Development and Testing of the Displaced-Solvent Functional on the Set of Cyclin Dependent Kinase 2 Congeneric Inhibitor Pairs In light of the excellent performance of the described subject matter at describing the binding thermodynamics of aa congeneric inhibitor pairs, two critical questions remained: (1) would the functional form of the DSF be appropriate to describe the binding thermodynamics of congeneric inhibitor pairs binding to other protein receptors, and (2) would there exist a consensus parameterization of the DSF that would well describe the binding thermodynamics of congeneric ligand pairs binding to an arbitrary protein receptor. To investigate the first outstanding issue, the binding thermodynamics of CDK2 and its small molecule inhibitors was investigated.

Figure 13:
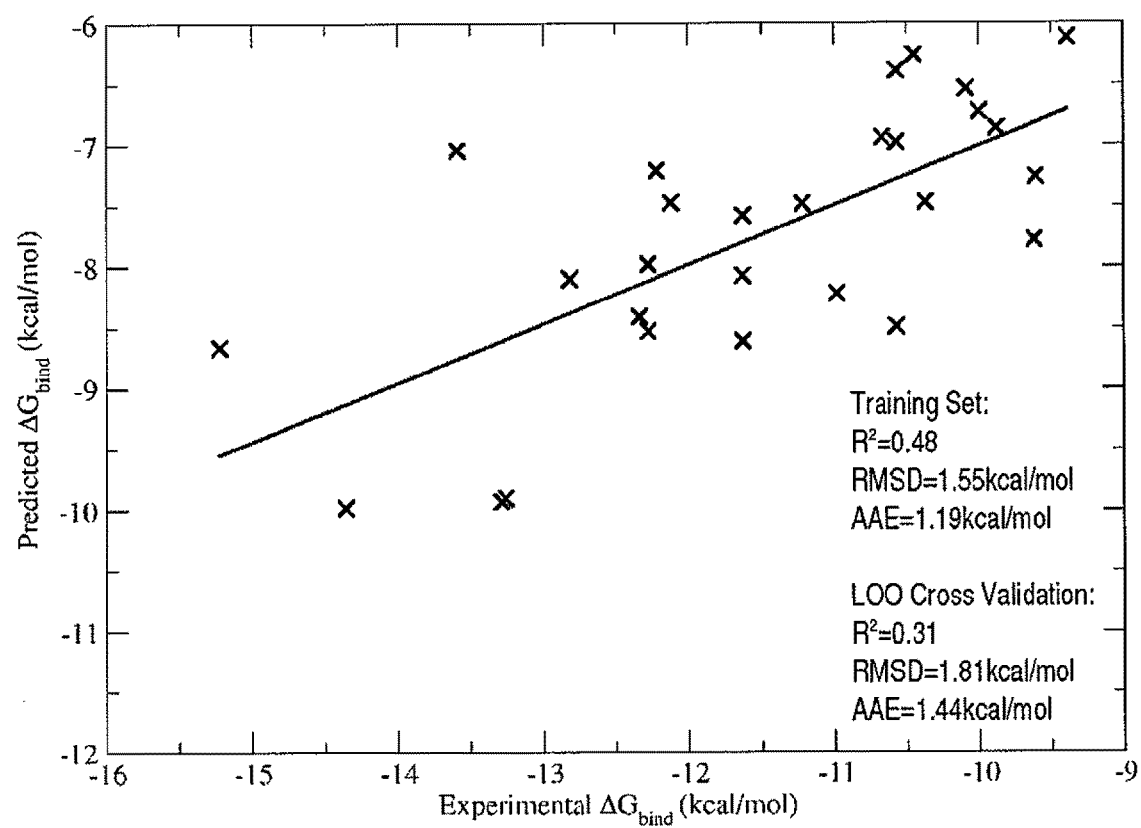
FIG. 13 is a depiction according to some embodiments of the described subject matter. Those hydration sites expected to contribute favorably to binding when evacuated by the ligand are here shown within the CDK2 active site in wire frame. Those expected to contribute energetically are shown in gray, those expected to contribute entropically are shown in green, and those expected to contribute energetically and entropically are shown in purple. Those hydrations sites discussed in the text are labeled in yellow.

The data for each hydration site identified in the CDK2 active site is presented in Table 7 and the resulting hydration site map is depicted in FIG. 13. This hydration site map elucidated several features of the experimentally known SAR of the CDK2 ligands. The active site of CDK2 is roughly planar and is typically bound by aromatic planar ligands. The active site pocket is lined above and below the plane of FIG. 13 by hydrophobic groups, and along the circumference of the plane by hydrogen bonding groups of the protein. As depicted in FIG. 13, the backbone hydrogen bonding sites Glu82, Phe83, and Leu84 are at the rear "hinge" region of the pocket, and charged residues Glu52, Lys34, Asp 146, Asp87, and Lys90 are at the front opening of the pocket. The hydration site map generated by the described subject matter correctly identifies that the hydrophobic enclosure above and below the plane of the active site, as depicted in FIG. 13, causes the active site solvent to be quite energetically depleted, as shown by the large number of gray hydration sites, which creates a high affinity for hydrophobic ligand groups in that region. The described subject matter also correctly identifies that those hydration sites solvating the hydrogen bonding sites in the hinge region of the active site lined by Glu82, Phe83, and Leu84 are especially favorable to evacuate. Hydration sites 3 and 5 are especially notable here, since nearly all CDK2 ligands that bind with high affinity make hydrogen bonds with residues Glu82 and Leu84, which are solvated by these hydrations sites. The described subject matter makes clear why this is the case. The solvent hydrating hydrogen bonding sites of Glu82 and Leu84 has very high excess chemical potential, thus favoring its transfer to the bulk fluid when evacuated by a cognate ligand.

Figure 14:
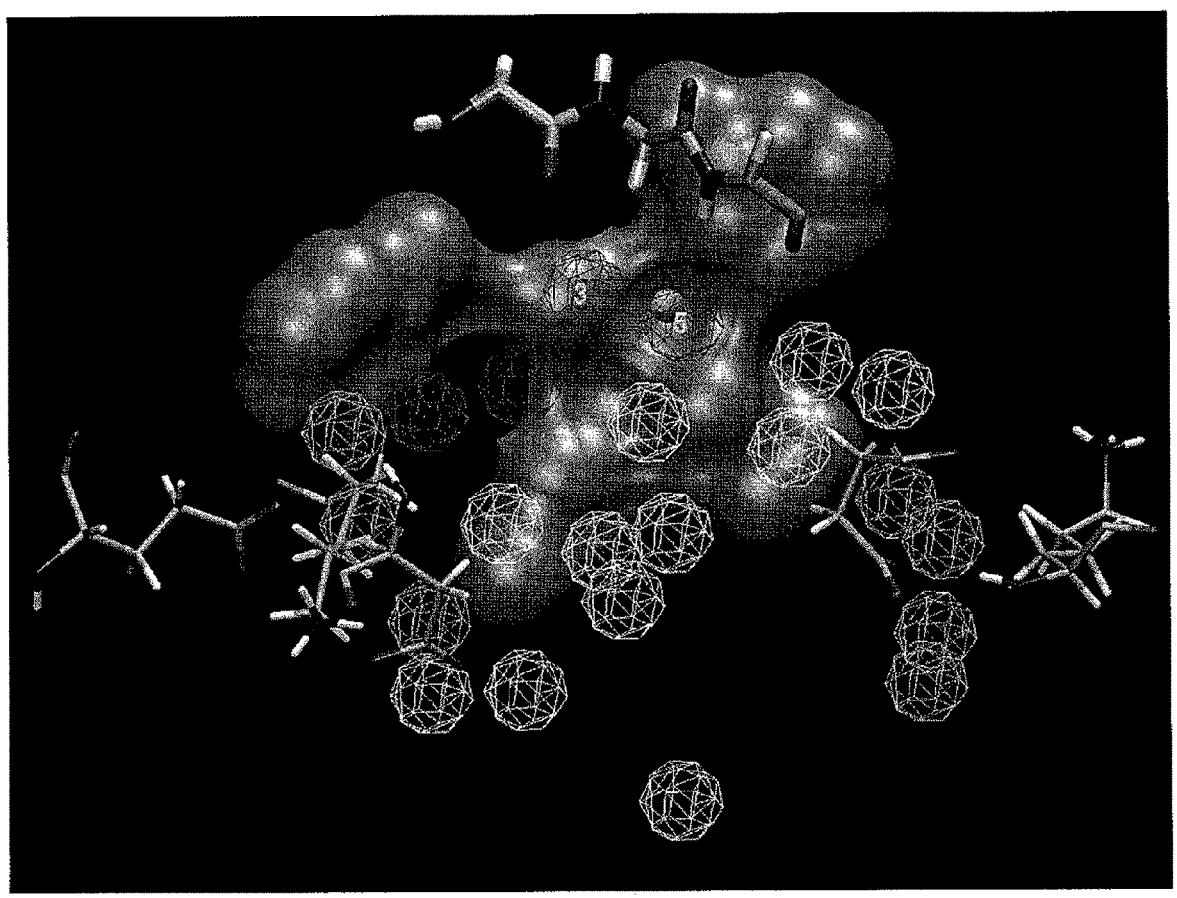
FIG. 14 is a depiction according to some embodiments of the described subject matter. The depiction concerns computed relative activities using the 5-parameter form of equation 2 versus experimental relative activities of the 47 congeneric inhibitor pairs with CDK2.
Figure 15:
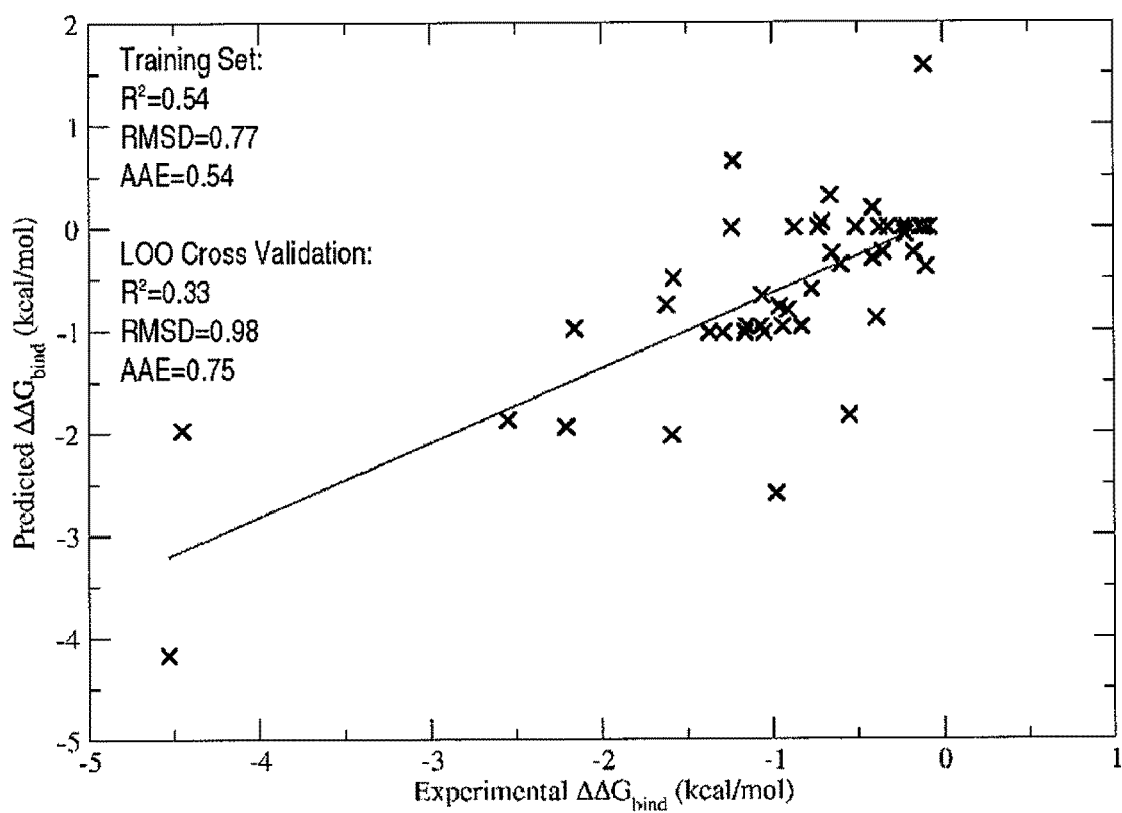
FIG. 15 is a depiction according to some embodiments of the described subject matter. The depiction concerns computed relative activities using the 3-parameter form of equation 2 versus experimental relative activities of the 47 congeneric inhibitor pairs with CDK2.

A dataset of 47 congeneric inhibitor pairs of CDK2 (see subsection TLC) (Table 8) was prepared. These 47 congeneric inhibitor pairs were pairs of CDK2 ligands that differed by at most three chemical groups and were prepared by a procedure analogous to that used to assemble the set of 31 congeneric inhibitor pairs of fXa. The parameters of the displaced -solvent functionals were optimized to reproduce the experimentally measured differences in binding affinity between each of these congeneric ligand pairs. The error of the resulting functionals were also estimated with leave-one-out cross validation. The resulting values of the parameters can be found in table 9 and plots of the predicted differences in binding free energy versus the experimental values are shown in FIGS. 14 and 15. The agreement of the predictions of the functionals with the experimental data was favorable: the Pearson correlation coefficient ($R^2$) was 0.53 and 0.54 for the 3-parameter and 5-parameter functionals, respectively. Under leave-one-out cross-validation, the $R^2$ value degraded to 0.37 and 0.33, respectively. The agreement for fXa was more favorable largely due to the tendency of the charged side chains at the front of the CDK2 pocket to reorganize to accommodate the particular bound ligand. However, from the reasonably good numerical agreement observed over the 5 kcal/mol free energy range of modifications plotted in FIGS. 14 and 15, this technique differentiated modifications that make large contributions to the binding affinity from modifications that merely make small contributions to the binding affinity for the CDK2 test system. This suggests that the present subject matter has sufficient flexibility in its functional form to describe the binding thermodynamics of ligands to a variety of protein receptors. It also directly motivates a study of whether or not a transferable parameterization of the DSF might be obtained that would have good predictive power for both CDK2, fXa, and other proteins.

Figure 16:
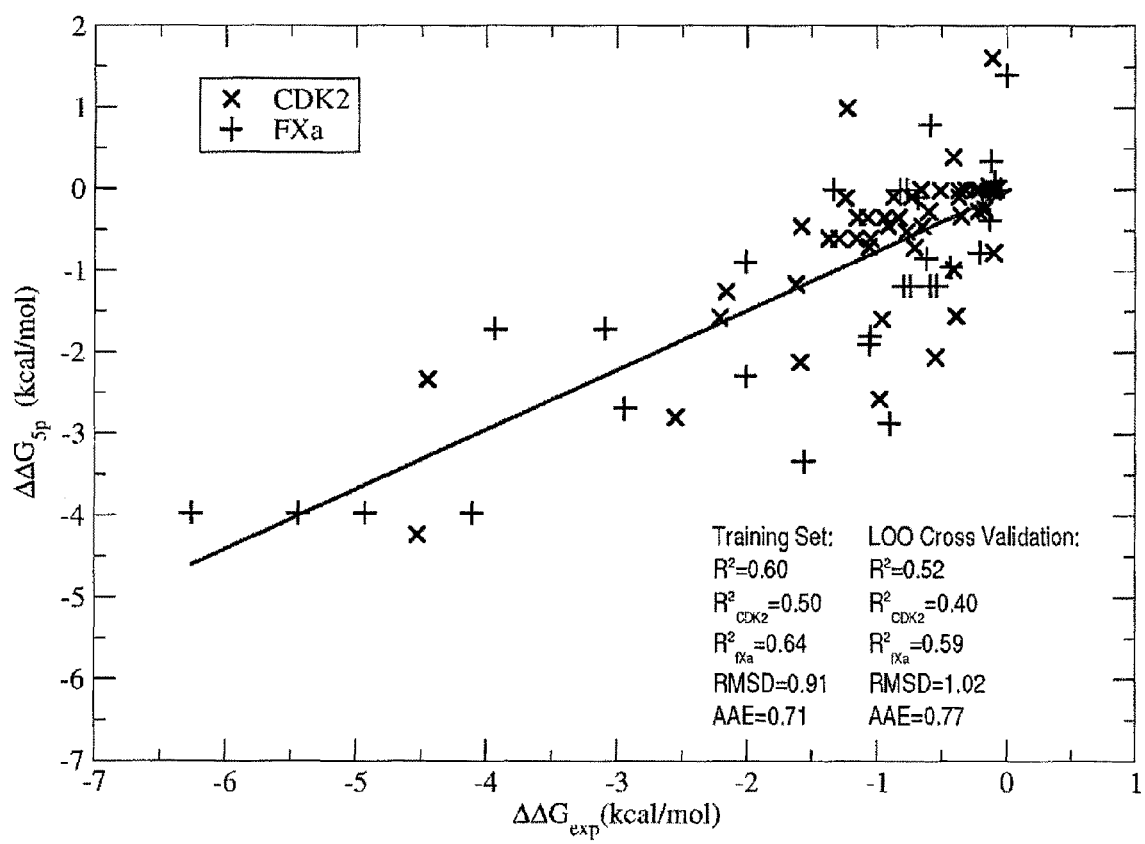
FIG. 16 is a depiction according to some embodiments of the described subject matter. The depiction concerns computed relative activities using the 5-parameter form of equation 2 versus experimental relative activities of the 78 congeneric inhibitor pairs with Factor Xa and CDK2.
Figure 17:
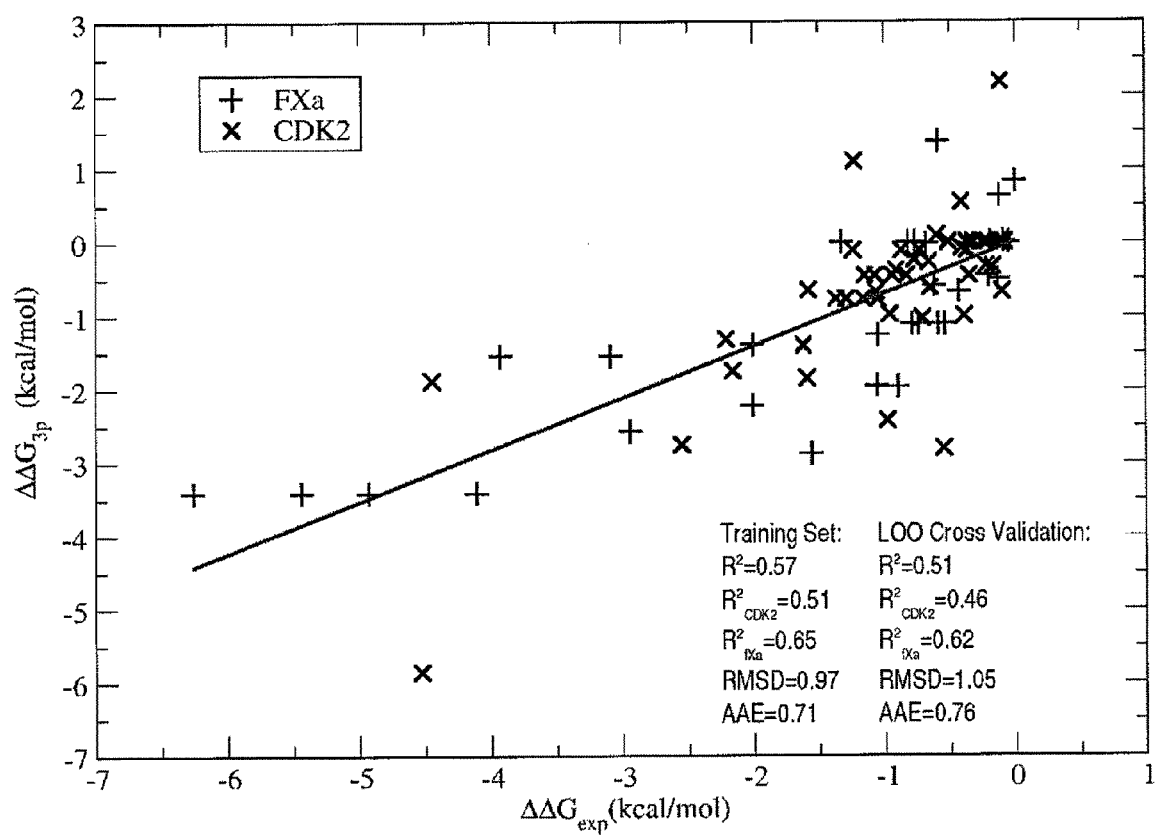
FIG. 17 is a depiction according to some embodiments of the described subject matter. The depiction concerns computed relative activities using the 3-parameter form of equation 2 versus experimental relative activities of the 78 congeneric inhibitor pairs with Factor Xa and CDK2.

F. Performance of the Displaced Solvent Functional for the Set of all Factor Xa and Cyclin Dependent Kinase 2 Congeneric Inhibitor Pairs To test whether or not a transferable parameterization of the DSF might exist that would have predictive utility for both the fXa and CDK2 systems, the 3-parameter and 5-parameter functionals were trained to the combined set of 31 fXa and 47 CDK2 congeneric inhibitor pairs. The functional was trained with the a forementioned techniques and estimated the error of the resulting functionals with leave-one-out cross validation. The resulting values of the parameters can be found in Table 10 and plots of the predicted differences in binding free energy versus the experimental values are shown in FIGS. 16 and 17. The agreement of the predictions of the functionals with the experimental data was favorable in light of the fact that it is spread across two very different protein receptors. The Pearson correlation coefficient ($R^2$) for the combined data set was 0.57 and 0.60 for both the 3-parameter and 5-parameter functionals. Under leave-one-out cross-validation, the $R^2$ value merely degraded to 0.52 and 0.51, respectively. Importantly, the high correlation is not due to one system being very well modeled and the other being poorly modeled. The consensus parameterization of the 3-parameter and 5-parameter functionals had $R^2$ values 0.64 and 0.65 over the fXa data, and $R^2$ values 0.50 and 0.51 over the CDK2 data. Thus, the consensus fit to both the CDK2 and fXa data merely marginally degrades the performance of the functionals for either system. Given the high ratio of data point to parameters, approximately 20:1, it is not surprising that these findings are quite robust under cross validation and reparameterization. This suggests quite strongly the physical picture suggested by the DSF—i.e., the molecular description of the thermodynamics of the displaced solvent is of crucial importance to understanding the binding affinity of congeneric ligands binding to a given receptor—is fundamentally correct.

Results suggest that the expulsion of active site water impacts protein-ligand binding affinities in 2 ways: (1) hydrophobic ligand groups that displace water from energetically unfavorable (hydrophobically enclosed) environments contribute enthalpically since the water molecules will make more favorable interactions in the bulk fluid; and (2) ligand groups that displace entropically structured solvent contribute even when the solvent interacts favorably with the protein since well-designed ligands will recapture the protein-water interaction energy. Congeneric inhibitor pairs 2J4I:38-2J4I:GSJ and 2BMG:25-2BMG:I1H are particularly clear examples where the expulsion of active site water that solvates an energetically unfavorable environment leads to large favorable contributions to the binding free energy. In contrast, congeneric pair 1MQ5:XLC-1MQ6:XLD offered an example of the expulsion of water from a hydration site with a favorable interaction energy and unfavorable excess entropy. The expulsion of water from this hydration site was found to be favorable, by the empirical criteria, presumably because the ligand group that displaces this water does a reasonably good job recapturing the interaction energy of the solvent with the protein with less entropic cost. Congeneric inhibitor pair 2BQ7:IID-2BQW:IIE illustrated that these two solvent categories, energetically unfavorable and entropically unfavorable, are by no means mutually exclusive and that the evacuation of solvent from the protein active site will often make both entropic and enthalpic contributions to the binding free energy. Important to the analysis is the assumption of complementarity—that is, that the difference between the water-protein energetic interactions and the ligand-protein interactions was expected to be small. This assumption is valid when the ligands form hydrogen bonds with the protein where appropriate and hydrophobic contacts otherwise; however, the congeneric ligand pair 1NFX:RDR/1NFW:RRR illustrated ligands that violate this hypothesis will often be mistreated by the technique. This has relevance to modern drug design since it suggests that it is misleading to look at particular crystal waters as favorable or unfavorable to displace, as is often done in structure based drug design. Instead, it can be more productive to consider how thermodynamically favorable displacing a crystal water will be when it is displaced by a complementary chemical group of a ligand.

The empirical functionals developed were suited to quantifying the contributions to the free energy of binding due to the ligand evacuating energetically unfavorable and entropically structured solvent for the set of congeneric pairs. It was able to differentiate those modifications to an existing ligand scaffold that made small contributions to the binding affinity of the complex from those modifications that made large contributions over a 6 kcal/mol range. Although these functionals can be readily tuned to well describe the binding thermodynamics for a single system, they can also be tuned to correctly describe the binding thermodynamics of several unrelated systems with high accuracy, suggesting that the parameters derived in section III.F can be readily transferable to other protein receptor systems aside from those studied here.

In their present form, the 3- and 5-parameter functionals can be useful to lead optimization, since the functionals appeared to well describe the thermodynamics of adding small chemical groups to a given ligand scaffold that are complementary to the protein surface. The performance of the functionals on the set of 28 crystal structure ligands suggests that terms of this type make large contributions to binding; however, these functionals should not be used as a stand alone tool for computational screening of chemically diverse compounds. The reason for this can be apparent: the displaced-solvent functionals presented here neglect several terms which will vary considerably over sets of chemically diverse ligands. These terms include the protein-ligand interaction energy, ligand solvation free energy, ligand configurational entropy, and the protein-reorganization free energy. Thus, a functional designed for computational screening can include additional terms describing these types of contributions to the free energy in addition to those contributions captured by the displaced-solvent functional.

In one embodiment, a clustering algorithm was designed to partition the displaced solvent density into spheres with optimal convergence properties for the inhomogeneous solvation theory analysis. This algorithm cycles through the positions of the oxygen atom of every water molecule found in the active site solvent density distribution and finds the position that has the greatest number of water neighbors within a 1 Å radius. This position was denoted a hydration site and all of the oxygen positions within 1 Å of it in the solvent density distribution was removed. This process is then repeated, cycling through the remaining positions. This loop is terminated when the clustering algorithm identifies a hydration site with a water-oxygen occupancy less than twice the expected value of a 1 Å radius sphere in the bulk fluid.

In one embodiment, in pseudocode, the clustering algorithm was implemented (hereinafter "Algorithm I") as

```
BEGIN CLUSTERING LOOP
    FOR ALL water molecules currently in the active site solvent
    distribution
        COMPUTE number of neighboring waters within 1 Å (oxygen
        to oxygen distance)
        SAVE coordinates of the water with the greatest number of
        neighbors as a cluster
        REMOVE all waters within 1 Å of this cluster center from
        the solvent density distribution
        IF the number of waters in this cluster is less than twice bulk
        density,
        THEN terminate and delete the last saved cluster
        ELSE repeat the loop
END LOOP
```

In one embodiment, the calculation of the excess entropies of the water molecules occupying the hydration sites was performed by numerically integrating an expansion of the entropy in terms of orientational and spatial correlation functions. The translational contribution was numerically integrated to the excess entropy in spherical coordinates using a length of 0.03 Å along r, 15° along θ, and 30° along φ; and the orientational contribution was numerically integrated with 10° along each Euler angle.

In one embodiment, in pseudocode, one implementation (hereinafter "Algorithm II") of the calculation of the translational component of the excess entropy of the water molecules in a given cluster was

```
COMPUTE r, θ, and φ for each water oxygen in the cluster
(the center of the cluster is used as the origin HISTOGRAM the
observed r, θ, and φ values in bins of 0.03 Å along r, 15° along θ,
and 30° along φ and save as N_{r,θ,φ}
DO r = 0, 1.0 Å, dr
    DO θ=0, 180°, dθ
        DO φ=0, 360°, dφ
            N_{r,θ,φ}=N_{r,θ,φ}/
            (r+dr/2)^2*sin(θ+dθ/2)*dr*dθ*dφ*#frames*ρ
            IF N_{r,θ,φ} ≠ 0 THEN
            S^e_{trans}=[N_{r,θ,φ}log(N_{r,θ,φ})]*
            (r+dr/2)^2*sin(θ+dθ/2)*dr*dθ*dφ+ S^e_{trans}
        END DO
    END DO
END DO
S^e_{trans}=-kρ*S^e_{trans}
```

In one embodiment, the integration of the orientational component of the excess entropy of the waters occupying a given hydration site is performed semi-analytically by way of a mixed quaternion/Euler angle formalism. Each water oxygen within the cluster is translated to a common reference point and the hydrogens are moved accordingly. The hydrogen to hydrogen mappings that allow for the smallest rotation of a water in the cluster onto the coordinates of a reference water are determined by a hydrogen to hydrogen distance criterion, i.e., $H_1 \to H_a$ and $H_2 \to H_b$ should be minimimal. The quaternion that maps $H_1 \to H_a$ using the rotational axis orthogonal to the $OH_1$ and $OH_a$ bond vectors is then determined. This rotation is applied and a second quaternion is determined that will rotate $H_2 \to H_b$ using the analogous orthogonal axis. These two quaternions are combined using the analytical combination rules to derive the single "master" quaternion that rotates $H_1 \to H_a$ and $H_2 \to H_b$ simultaneously. It should be noted the calculation of this quaternion can be done in a single stage using the axis of rotation orthogonal to vectors $H_1 H_a$ and $H_2 H_b$, but this technique suffered numerical instabilities when the vectors were close to parallel; so, the two-stage technique can be used. From the "master" quaternion the three Euler angles that rotate a cluster water onto the reference water were analytically extracted. This process was repeated for all waters and the rotational correlation function was determined from the distribution of the Euler angles and used to numerically integrate the one-body rotational term using a 10° discretization.

In one embodiment, In pseudocode, one implementation (hereinafter "Algorithm III") of the calculation of the orientational component of the excess entropy of the water molecules in a given cluster was

```
TRANSLATE each water oxygen to the origin, move all water hydrogens appropriately
SAVE the hydrogen positions of the first water in the distribution as the reference water, label H_a and H_b
LOOP FOR EACH water in the cluster
    COMPUTE the mapping of hydrogens H_1 and H_2 of the cluster water onto the reference water such that
dist(H_1,H_a) and dist(H_2,H_b) are minimal
    COMPUTE the axis of rotation A=H_1 × H_a where H_1 and H_a are the vectors from the origin to the relevant
hydrogen atom
        COMPUTE the angle of rotation α=-cos^{-1}[ (H_1·H_a) / (||H_1|| ||H_a||) ]
        COMPUTE the elements of quaternion q as
            q^0=cos((α/2)
            q^1=A_1*sin((α/2)
            q^2=A_2*sin((α/2)
            q^3=A_3*sin((α/2)
        ROTATE H_1 and H_2 with this quaternion via
            H_j^{(1)}=(q^0q^0+q^1q^1-q^2q^2-q^3q^3)H_j^{(1)}+2(q^1q^2+q^0q^3)H_j^{(2)}+2(q^1q^3+q^0q^2)H_j^{(3)}
            H_j^{(2)}=2(q^1q^2+q^0q^3)H_j^{(1)}+(q^0q^0-q^1q^1+q^2q^2-q^3q^3)H_j^{(2)}+2(q^2q^3+q^0q^1)H_j^{(3)}
            H_j^{(3)}=2(q^1q^3+q^0q^2)H_j^{(1)}+2(q^2q^3+q^0q^1)H_j^{(2)}+(q^0q^0-q^1q^1- q^2q^2+q^3q^3)H_j^{(3)}
        COMPUTE A=H_a/ ||H_a||
        COMPUTE V_1=H_b × A
        COMPUTE V_2=H_2 × A
        COMPUTE α=cos^{-1}[ (V_1·V_2) / (||V_1|| ||V_2||) ]
        COMPUTE V_3=V_1 × V_2
        IF V_3·A < 0.0 THEN α=-α
        COMPUTE the elements of quaternion w as
            w^0=cos(α/2)
            w^1=A_1*sin(α/2)
            w^2=A_2*sin(α/2)
            w^3=A_3*sin(α/2)
        COMPUTE the quaternion cross product e=q × w
        COMPUTE renormalize this quaternion as e= e /||e||
        COMPUTE the Euler angles of the rotation described by quaternion e as
            (=tan^{-1}(2(e^2e^3+e^0e^1)/(1-2(e^1e^1+e^2e^2)))
            θ=sin^{-1}(2(e^1e^3+e^0e^2))
            ψ=tan^{-1}(2(e^1e^2+e^0e^3)/(1-(e^2e^2+e^3e^3)))
        SAVE the Euler angles for each water
END LOOP
HISTOGRAM the observed φ, θ, and ψ values in 10° bins along each Euler angle and save as N_{φ,θ,ψ}
DO φ=0, 180°, dθ
    DO θ=0, 180°, dθ
        DO ψ=0, 180°, dθ
            IF N_{φ,θ,ψ} ≠ 0 THEN S^e_{rot}=[N_{φ,θ,ψ} log(N_{φ,θ,ψ})]*dφ *dθ*dψ+ S^e_{rot}
```

```
        END DO
      END DO
   END DO
$S^e_{trans} = -[(k*\#wat)/((*\#frames)]S^e_{trans}$
```

A dual color code is used to visualize the hydration sites against the backdrop of the protein so that the structural and thermodynamic properties, both energetic and entropic, of the hydration sites are immediately apparent in one summary figure. This visualization was performed by writing a PDB formatted file of the hydration sites. In this file replaced the occupancy and beta values with the excess entropy and average system interaction energy values for each hydration site. Many existing protein structure visualization programs contain the ability to visualize and color parts of the system differently based upon the specified beta and occupancy values. This allowed for the visualization of the hydration sites against the backdrop of the protein with the excess entropy and interaction energy related to the viewer by way of a color code.

Each hydration site in the active site volume was chosen to be viewed if either its average system interaction energy or its excess entropy were less favorable than some set of predefined cutoffs. If a hydration site was displayed merely because its average system interaction energy was less favorable than some cutoff, then this hydration site was visualized in silver; if a hydration site was displayed merely because its excess entropy was less favorable than some cutoff, then this hydration site was visualized in green; and if a hydration site was displayed because both its average system interaction energy and excess entropy were less favorable than some cutoffs, then this hydration site was visualized in purple. This visualization scheme allowed rapid viewing of several thermodynamic properties of the hydration sites simultaneously. An example of the resulting graphic can be found in FIG. 2, with example cutoff values suggested by FIG. 1.

The visualizations of the hydration sites were performed similarly here as above. However the differences in the structures of two congeneric ligands was also displayed by visualizing two identical replicas of the protein and hydration sites next two each other where one congeneric ligand was docked in the active site of protein replica 1 and another congeneric ligand was docked in the active site of protein replica two. Examples of the resulting graphics produced by this technique can be seen in FIGS. 5-10.

An empirical technique is use to determine whether or not and to what degree the solvent in a given hydration site is displaced from receptor by the bound ligand. This technique uses the Cartesian distances between the ligand atoms and the hydration sites to develop an approximate description of the evacuation of solvent from the hydration sites by a ligand. This technique works by noting that as a ligand atom approaches a hydration site the Van der Waals surface of the ligand atom will begin to displace solvent from the hydration site once the solvent in the hydration site and the ligand come in to contact; as the ligand atom moves closer to the hydration, more solvent will be evacuated. The form of the functional was a sum over ligand heavy atoms and a sum over hydration sites. The functional itself used to describe this effect was $$\Delta G_{lig} = \sum_{lig,hs} \Delta G_{rwd}(E_{hs}, S^e_{hs}) \left(1 - \frac{\bar{r}_{lig} - \bar{r}_{hs}}{R_{co}}\right) \Theta(R_{co} - |\bar{r}_{lig} - \bar{r}_{hs}|) \quad (4)$$

where $\Delta G_{bind}$ was the predicted binding free energy of the ligand, $\Delta G_{rwd}(E_{hs}, S^e_{hs})$ was the free energy contrition of evacuating the solvent from the hydration site hs to the binding affinity of the ligand, $R_{co}$ was the distance cutoff for a ligand atom beginning to displace a hydration site, and $\Theta$ was the Heaviside step function. Once a particular choice of $\Delta G_{rwd}(E_{hs}, S^e_{hs})$ is specified, the free parameter $R_{co}$ is tuned to reproduce the known binding thermodynamics of some large set of protein ligand complexes. Several choices of the function $\Delta G_{rwd}(E_{hs}, S^e_{hs})$ are possible. The most obvious is the transfer free energy of the solvent molecules in the hydration from the active site to the bulk fluid and corresponds to a arrangement of hard spheres in the shape of the ligand evacuating the solvent. This choice however neglect considering that "real" ligand will not interact with the proteins hard spheres. Thus the interactions of the protein and the ligand can be implicitly accounted for by using other choices for the function $\Delta G_{rwd}(E_{hs}, S^e_{hs})$.

As noted elsewhere, in one embodiment, the functional that was developed to describe the binding affinities of the ligands as a function of the thermodynamic properties hydration sites was eq. 1. The form of the functional was a sum over ligand heavy atoms and a sum over hydration sites. Each time a ligand heavy was found within some parameterized distance of a hydration site with an interaction energy or excess entropy predicted to be favorable to evacuate by some fit empirical criteria, an additive contribution was summed.

In pseudocode, this functional was implemented as

```
LOOP FOR EACH hydration site
    LOOP FOR EACH heavy atom of the ligand
        COMPUTE the distance between the particular
    hydration site (HS) and the ligand heavy atom (LA), i.e.,
        IF dist(HS,LA)
            IF S^e_hs > S_co THEN
                G_rwd.HS=G_rwd.HS-T*S_rwd*(1-(dist(HS,LA)/R_co))
            END IF
            IF E_hs > E_co THEN
                G_rwd.HS= G_rwd.HS+E_rwd*(1-(dist(HS,LA)/R_co))
            END IF
        END IF
    END LOOP
    G_bind= G_bind+G_rwd.HS
END LOO
```

Table and Figure Captions

TABLE 1

Calculated thermodynamic and local water structure data for each of the 43 hydration sites that were identified by clustering the factor Xa active site solvent density distribution. The occupancy was the number of water oxygen atoms found occupying a given hydration site during the 10 ns of molecular dynamics simulation, $-TS^e$ is the excess entropic contribution to the free energy calculated from a truncated expansion of the excess entropy in terms of correlations in the single particle translational and rotational density, E is average energy of interaction of the water molecules in a given hydration site with the rest of the system, the #nbrs value is the average number of neighboring waters found within a 3.5 Å oxygen atom to oxygen atom distance from a water occupying the specified hydrations site, the #HBnbrs value is the is the average number of neighboring water oxygens found within a 3.5 Å distance from the water oxygen occupying the specified hydrations site that make a less than 30° oxygen-oxygen-hydrogen hydrogen bonding angle with this water, the % HB value is the #HBnbrs/#nbrs fraction, and the exposure value is the #nbrs value divided by the bulk #nbrs value found in the bulk fluid.

| Hyd. Site | Occupancy | $-TSe$ (kcal/mol) | E (kcal/mol) | #nbrs | #HBnbrs | % HB | Exposure |
|---|---|---|---|---|---|---|---|
| Neat | 1385.00 | N/A* | −19.67 | 5.09 | 3.53 | 0.69 | 1.00 |
| 1 | 9347.00 | 4.00 | −20.34 | 1.54 | 1.30 | 0.84 | 0.30 |
| 2 | 9062.00 | 3.91 | −22.59 | 3.13 | 1.99 | 0.64 | 0.61 |
| 3 | 8425.00 | 2.61 | −20.85 | 3.45 | 2.27 | 0.66 | 0.68 |
| 4 | 8383.00 | 2.93 | −19.55 | 3.12 | 2.79 | 0.89 | 0.61 |
| 5 | 8157.00 | 3.24 | −23.18 | 2.52 | 1.88 | 0.75 | 0.50 |
| 6 | 8123.00 | 3.20 | −21.86 | 3.62 | 2.24 | 0.62 | 0.71 |
| 7 | 8116.00 | 3.37 | −21.82 | 3.22 | 2.12 | 0.66 | 0.63 |
| 8 | 8081.00 | 2.74 | −22.73 | 3.05 | 2.39 | 0.78 | 0.60 |
| 9 | 7257.00 | 2.13 | −19.38 | 4.30 | 2.76 | 0.64 | 0.84 |
| 10 | 7172.00 | 2.52 | −21.04 | 3.75 | 2.85 | 0.76 | 0.74 |
| 11 | 6886.00 | 2.05 | −20.71 | 3.41 | 2.24 | 0.66 | 0.67 |
| 12 | 6815.00 | 2.28 | −16.93 | 1.62 | 1.49 | 0.92 | 0.32 |
| 13 | 6238.00 | 1.72 | −17.88 | 2.72 | 2.05 | 0.75 | 0.53 |
| 14 | 6081.00 | 1.95 | −19.89 | 2.58 | 2.11 | 0.82 | 0.51 |
| 15 | 5441.00 | 1.83 | −22.62 | 4.66 | 3.63 | 0.78 | 0.92 |
| 16 | 5078.00 | 1.51 | −20.01 | 3.30 | 2.56 | 0.78 | 0.65 |
| 17 | 4919.00 | 1.33 | −17.04 | 2.45 | 1.78 | 0.73 | 0.48 |
| 18 | 4887.00 | 1.35 | −17.74 | 3.38 | 2.46 | 0.73 | 0.66 |
| 19 | 4466.00 | 1.20 | −19.48 | 4.11 | 2.77 | 0.67 | 0.81 |
| 20 | 4386.00 | 1.37 | −22.14 | 3.69 | 2.79 | 0.76 | 0.72 |
| 21 | 4356.00 | 1.23 | −18.50 | 3.75 | 2.67 | 0.71 | 0.74 |
| 22 | 4241.00 | 1.22 | −20.27 | 3.72 | 2.63 | 0.71 | 0.73 |
| 23 | 4189.00 | 1.13 | −19.58 | 3.87 | 2.84 | 0.73 | 0.76 |
| 24 | 4170.00 | 1.17 | −19.64 | 3.69 | 2.51 | 0.68 | 0.72 |
| 25 | 4137.00 | 1.12 | −20.85 | 4.61 | 2.59 | 0.56 | 0.91 |
| 26 | 4067.00 | 1.07 | −20.19 | 4.23 | 3.09 | 0.73 | 0.83 |
| 27 | 4046.00 | 1.03 | −20.72 | 4.37 | 3.48 | 0.80 | 0.86 |
| 28 | 3921.00 | 1.10 | −16.74 | 2.66 | 2.00 | 0.75 | 0.52 |
| 29 | 3833.00 | 1.03 | −21.44 | 4.27 | 2.57 | 0.60 | 0.84 |
| 30 | 3793.00 | 1.04 | −21.97 | 4.05 | 2.68 | 0.66 | 0.80 |
| 31 | 3786.00 | 0.99 | −20.00 | 4.70 | 3.39 | 0.72 | 0.92 |
| 32 | 3686.00 | 0.99 | −22.61 | 4.48 | 2.69 | 0.60 | 0.88 |
| 33 | 3618.00 | 1.00 | −20.46 | 4.34 | 2.56 | 0.59 | 0.85 |
| 34 | 3570.00 | 0.95 | −19.75 | 4.36 | 2.92 | 0.67 | 0.86 |
| 35 | 3312.00 | 0.90 | −24.24 | 4.41 | 2.74 | 0.62 | 0.87 |
| 36 | 3296.00 | 0.84 | −19.66 | 4.06 | 2.66 | 0.66 | 0.80 |
| 37 | 3152.00 | 0.79 | −18.87 | 4.57 | 3.15 | 0.69 | 0.90 |
| 38 | 3094.00 | 0.73 | −19.09 | 4.70 | 3.25 | 0.69 | 0.92 |
| 39 | 3089.00 | 0.92 | −21.61 | 3.55 | 2.55 | 0.72 | 0.70 |
| 40 | 3007.00 | 0.79 | −19.96 | 4.20 | 2.79 | 0.67 | 0.82 |
| 41 | 3003.00 | 0.78 | −20.41 | 3.71 | 2.70 | 0.73 | 0.73 |
| 42 | 2862.00 | 0.73 | −19.26 | 4.72 | 3.28 | 0.69 | 0.93 |
| 43 | 2791.00 | 0.75 | −20.93 | 3.98 | 2.84 | 0.71 | 0.78 |

*The truncated expansion of the excess entropy used merely included the first order terms. The first order excess entropic term for all neat fluids is strictly zero, however the second order and larger terms can be quite large.

TABLE 2

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1MQ5:XLC | | 1MQ6:XLD | | −2.94 | −2.85 | −2.54 |
| 1NFU:RRP | | 1NFY:RTR | | −1.56 | −2.56 | −2.98 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id)x(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1NFX:RDR | | 1NFW:RRR | | −0.59 | 1.35 | 0.94 |
| 2BMG:25 | | 2BMG:28 | | −0.62 | −0.61 | −0.62 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2BMG:25 | | 2BMG:I1H | | −1.05 | −1.31 | −1.31 |
| 2BMG:28 | | 2BMG:I1H | | −0.43 | −0.70 | −0.69 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id)x(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1KYE:3 | 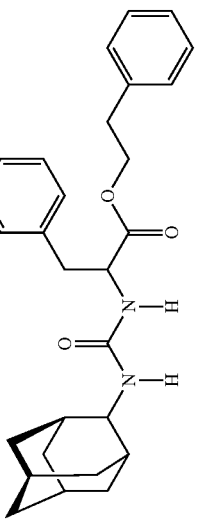 | 1KYE:2 | 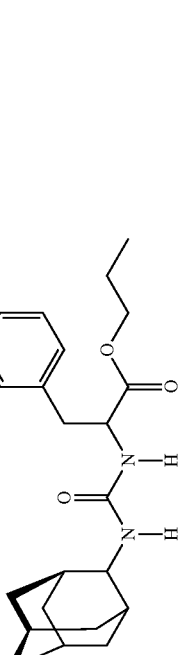 | −0.90 | −2.05 | −2.34 |
| 1V3X:56 | 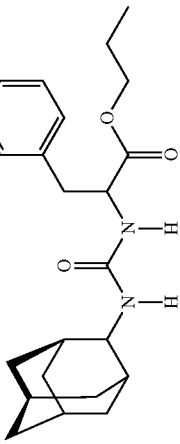 | 1V3X:57 |  | −0.59 | −1.15 | −1.12 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1V3X:60 | | 1V3X:56 | | −0.19 | 0.00 | 0.00 |
| 1V3X:56 | | 1V3X:D76 | | −0.54 | −1.15 | −1.12 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1V3X:60 | | 1V3X:57 | | −0.79 | −1.15 | −1.12 |
| 1V3X:D76 | | 1V3X:57 | | −0.05 | 0.00 | 0.00 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id)x(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1V3X:60 | | 1V3X:D76 | | −0.74 | −1.15 | −1.12 |
| 2BQ7:IID | | 2BQW:IIE | | −2.01 | −1.73 | −1.95 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id)x(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2BQ7:IID |  | 2BOH:IIA |  | −2.01 | −1.80 | −2.09 |
| 2BQW:IIE |  | 2BOH:IIA |  | 0.00 | −0.07 | −0.13 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1Z6E:I1a | | 1Z6E:43 | | −0.09 | 0.04 | 0.39 |
| 1Z6E:43 | | 1Z6E:IK8 | | −0.68 | −0.04 | −0.45 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id)x(ligand residue name):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1Z6E:I1a | | 1Z6E:IK8 | | −0.77 | 0.00 | −0.06 |
| 1G2L:T87 | | 1G2M:R11 | | −0.21 | 0.79 | 0.20 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1KSN:5c | | 1KSN:FXV | | −0.13 | −0.87 | −0.78 |
| 2FZZ:4QC | | 2G00:5QC | | −1.06 | −1.70 | −1.68 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand name)"; and when the ligand was built from congeneric series data, the ligand was designated "(template pdb id)x(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1LQD:107 | | 1LQD:CMI | | −3.93 | −2.52 | −2.48 |
| 1LQD:108 | | 1LQD:46 | | −3.09 | −2.52 | −2.48 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1F0R:815 | | 1F0S:PR2 | | −0.12 | 0.09 | 0.14 |
| 2J4I:33 | | 2J4I:GSJ | | −0.82 | 0.00 | 0.00 |
| 2J4I:32 | | 2J4I:GSJ | | −4.93 | −4.87 | −4.83 |
| 2J4I:38 | | 2J4I:GSJ | | −6.26 | −4.87 | −4.83 |

TABLE 2-continued

Inhibition data for the congeneric ligand pairs binding to factor Xa and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2J4I:32 | | 2J4I:33 | | −4.11 | −4.87 | −4.83 |
| 2J4I:38 | | 2J4I:33 | | −5.44 | −4.87 | −4.83 |
| 2J4I:38 | | 2J4I:32 | | −1.33 | 0.00 | 0.00 |

TABLE 3

The optimized parameters for the 3-parameter and 5-parameter forms of the displaced-solvent functional trained to reproduce the experimentally measured differences in binding affinity of 31 fXa congeneric pairs.

| Parameters: | $R_{co}$ (Å) | $E_{rwd}$ (kcal/mol) | $-TS_{rwd}$ (kcal/mol) | $E_{co}$ (kcal/mol) | $TS_{co}$ (kcal/mol) |
|---|---|---|---|---|---|
| version 3p | 2.8  | −0.99 | −0.99 | −18.91 | 1.34 |
| version 5p | 3.27 | −0.92 | −0.66 | −18.89 | 1.34 |

TABLE 4

Inhibition data for the 28 ligands extracted from solved crystal structures binding to factor Xa and the predicted activity differences from the trained 3-parameter and 5-parameter displaced-solvent functionals. Each ligand was designated "(pdb id):(ligand residue name)"

| Ligand | $\Delta G_{exp}$ (kcal/mol) | $\Delta G_{3p}$ (kcal/mol) | $\Delta G_{5p}$ (kcal/mol) |
|---|---|---|---|
| 2BOK:784 | −9.39 | −6.12 | −7.24 |
| 2J2U:GSQ | −9.61 | −7.26 | −8.60 |
| 2BQ7:IID | −9.62 | −7.78 | −8.77 |
| 1G2L:T87 | −9.88 | −6.86 | −8.93 |
| 2J34:GS5 | −10.00 | −6.73 | −7.80 |
| IG2M:R11 | −10.09 | −6.54 | −8.42 |
| 1KYE:RUP | −10.37 | −7.47 | −8.88 |
| 1F0R:815 | −10.45 | −6.26 | −7.53 |
| 1F0S:PR2 | −10.57 | −6.39 | −7.77 |
| 2BMG:I1H | −10.57 | −8.49 | −9.34 |
| 1NFU:RRP | −10.57 | −6.98 | −8.50 |
| 2J38:GS6 | −10.67 | −6.94 | −8.06 |
| 1LQD:CMI | −10.98 | −8.22 | −9.30 |
| 2CJI:GSK | −11.22 | −7.48 | −8.52 |
| 2BQW:IIE | −11.63 | −8.07 | −9.16 |
| 1NFX:RDR | −11.63 | −7.58 | −8.97 |
| 2BOH:IIA | −11.63 | −8.61 | −9.72 |
| 1NFY:RTR | −12.12 | −7.47 | −8.89 |
| 1NFW:RRR | −12.22 | −7.21 | −8.46 |
| 1MQ5:XLC | −12.28 | −8.53 | −9.58 |
| 2J4I:GSJ | −12.28 | −7.98 | −9.33 |
| 1EZQ:RPR | −12.34 | −8.41 | −9.91 |
| 1KSN:FXV | −12.82 | −8.10 | −9.39 |
| 1Z6E:IK8 | −13.26 | −9.90 | −11.55 |
| 2FZZ:4QC | −13.29 | −9.93 | −11.33 |
| 1FJS:Z34 | −13.59 | −7.04 | −8.75 |
| 2G00:5QC | −14.36 | −9.98 | −11.44 |
| 1MQ6:XLD | −15.22 | −8.66 | −9.75 |

TABLE 5

The optimized parameters for the 3-parameter and 5-parameter forms of the displaced-solvent functional trained on the set of 28 ligands taken from factor Xa crystal structures.

| Parameters: | $R_{co}/$ (Å) | $E_{rwd}/$(kcal/mol) | $-TS_{rwd}/$ (kcal/mol) | $E_{co}/$ (kcal/mol) | $TS_{co}/$ (kcal/mol) |
|---|---|---|---|---|---|
| version 3p | 2.8  | −0.42 | −0.42 | −16.87 | 0.99 |
| version 5p | 2.52 | −0.2  | −0.44 | −19.62 | 1.18 |

TABLE 6

Results of the 3- and 5-parameter displaced-solvent functionals trained on the set 31 congeneric pairs applied to the 28 ligand set; and results of the 3-parameter and 5-parameter displaced-solvent functionals trained on the 28 ligand set applied to the set of 22 congeneric pair subset that excludes congeneric pairs where both pairs are crystal structure ligands.

| | 3 Parameter Form | |
|---|---|---|
| Status | 31 Congeneric Pairs Trained | 28 Crystal Structure Ligands Tested |
| RMSD/(kcal/mol) | 0.76 | 3.19 |
| AAE/(kcal/mol) | 0.60 | 2.60 |
| $R^2$ | 0.81 | 0.17 |

| | 5 Parameter Form | |
|---|---|---|
| Status | 31 Congeneric Pairs Trained | 28 Crystal Structure Ligands Tested |
| RMSD/(kcal/mol) | 0.75 | 3.09 |
| AAE/(kcal/mol) | 0.58 | 2.53 |
| $R^2$ | 0.81 | 0.17 |

| | 3 Parameter Form | |
|---|---|---|
| Status | 28 Crystal Structure Ligands Trained | 22 Congeneric Pairs Tested |
| RMSD/(kcal/mol) | 1.56 | 1.99 |
| AAE/(kcal/mol) | 1.17 | 1.24 |
| $R^2$ | 0.48 | 0.53 |

| | 5 Parameter Form | |
|---|---|---|
| Status | 28 Crystal Structure Ligands Trained | 22 Congeneric Pairs Tested |
| RMSD/(kcal/mol) | 1.51 | 1.88 |
| AAE/(kcal/mol) | 1.18 | 1.17 |
| $R^2$ | 0.50 | 0.59 |

TABLE 7

Calculated thermodynamic and local water structure data for each of the 43 hydration sites that were identified by clustering the CDK2 active site solvent density distribution. The occupancy was the number of water oxygen atoms found occupying a given hydration site during the 10 ns of molecular dynamics simulation, $-TS^e$ is the excess entropic contribution to the free energy calculated from a truncated expansion of the excess entropy in terms of correlations in the single particle translational and rotational density, E is average energy of interaction of the water molecules in a given hydration site with the rest of the system, the #nbrs value is the average number of neighboring waters found within a 3.5 Å oxygen atom to oxygen atom distance from a water occupying the specified hydrations site, the #HBnbrs value is the is the average number of neighboring water oxygens found within a 3.5 Å distance from the water oxygen occupying the specified hydrations site that make a less than 30° oxygen-oxygen-hydrogen hydrogen bonding angle with this water, the % HB value is the #HBnbrs/#nbrs fraction, and the exposure value is the #nbrs value divided by the bulk #nbrs value found in the bulk fluid.

| Hyd. Site | Occupancy | $-TS^e$ (kcal/mol) | E (kcal/mol) | #nbrs | #HBnbrs | % HB | Exposure |
|---|---|---|---|---|---|---|---|
| Neat | 1385 | N/A* | −19.67 | 5.09 | 3.53 | 0.69 | 1 |
| 1 | 9608 | 4.23 | −20.66 | 1.70 | 0.88 | 0.33 | 0.25 |
| 2 | 9327 | 4.05 | −22.16 | 2.86 | 1.37 | 0.56 | 0.39 |
| 3 | 9062 | 3.50 | −18.57 | 2.12 | 1.89 | 0.42 | 0.53 |
| 4 | 8570 | 3.19 | −22.97 | 3.33 | 2.03 | 0.65 | 0.57 |
| 5 | 7983 | 2.67 | −18.23 | 2.49 | 2.09 | 0.49 | 0.59 |
| 6 | 7669 | 2.43 | −23.19 | 4.63 | 2.60 | 0.91 | 0.74 |
| 7 | 7646 | 2.62 | −18.31 | 3.29 | 2.83 | 0.65 | 0.80 |
| 8 | 7467 | 2.56 | −24.27 | 3.97 | 1.82 | 0.78 | 0.51 |
| 9 | 7133 | 2.94 | −24.32 | 3.35 | 1.85 | 0.66 | 0.52 |
| 10 | 6888 | 1.98 | −18.6 | 3.45 | 3.03 | 0.68 | 0.86 |
| 11 | 6869 | 2.41 | −24.14 | 2.98 | 1.90 | 0.58 | 0.54 |
| 12 | 6167 | 1.91 | −18.63 | 2.65 | 2.20 | 0.52 | 0.62 |
| 13 | 5719 | 1.66 | −20.59 | 3.61 | 1.96 | 0.71 | 0.56 |
| 14 | 5719 | 1.66 | −20.59 | 3.61 | 1.96 | 0.71 | 0.56 |
| 15 | 5584 | 1.52 | −18.7 | 4.15 | 3.05 | 0.82 | 0.86 |
| 16 | 5552 | 1.77 | −22.73 | 3.37 | 2.12 | 0.66 | 0.60 |
| 17 | 5411 | 1.60 | −23.05 | 3.69 | 2.18 | 0.73 | 0.62 |
| 18 | 5021 | 1.45 | −23.14 | 3.33 | 1.95 | 0.65 | 0.55 |
| 19 | 4851 | 1.49 | −23.09 | 4.71 | 2.72 | 0.93 | 0.77 |
| 20 | 4812 | 1.44 | −21.11 | 3.86 | 2.73 | 0.76 | 0.77 |
| 21 | 4790 | 1.29 | −19.93 | 4.07 | 2.85 | 0.80 | 0.81 |
| 22 | 4764 | 1.28 | −17.7 | 3.83 | 2.96 | 0.75 | 0.84 |
| 23 | 4549 | 1.16 | −19.24 | 3.93 | 3.16 | 0.77 | 0.90 |
| 24 | 4450 | 1.12 | −19.35 | 3.82 | 2.96 | 0.75 | 0.84 |
| 25 | 3946 | 1.05 | −21.42 | 3.59 | 2.59 | 0.71 | 0.73 |
| 26 | 3715 | 1.01 | −20.43 | 3.50 | 1.83 | 0.69 | 0.52 |
| 27 | 3687 | 1.06 | −19.71 | 3.95 | 2.66 | 0.78 | 0.75 |
| 28 | 3676 | 1.01 | −23.12 | 4.51 | 2.68 | 0.89 | 0.76 |
| 29 | 3608 | 1.03 | −22.82 | 5.08 | 2.19 | 1.00 | 0.62 |
| 30 | 3580 | 0.95 | −20.49 | 4.53 | 3.24 | 0.89 | 0.92 |
| 31 | 3523 | 0.91 | −17 | 3.31 | 2.48 | 0.65 | 0.70 |
| 32 | 3388 | 0.91 | −20.89 | 4.34 | 2.90 | 0.85 | 0.82 |
| 33 | 3303 | 0.86 | −19.88 | 4.80 | 3.11 | 0.94 | 0.88 |
| 34 | 3348 | 0.93 | −21.86 | 4.37 | 2.39 | 0.86 | 0.68 |
| 35 | 3271 | 0.92 | −22.85 | 5.06 | 2.64 | 0.99 | 0.75 |
| 36 | 3250 | 0.84 | −17.2 | 3.53 | 2.75 | 0.69 | 0.78 |
| 37 | 3199 | 0.83 | −19.86 | 4.34 | 3.51 | 0.85 | 0.99 |
| 38 | 3092 | 0.77 | −19.01 | 4.58 | 3.26 | 0.90 | 0.92 |
| 39 | 3074 | 0.80 | −19.71 | 4.73 | 3.37 | 0.93 | 0.95 |
| 40 | 3017 | 0.78 | −18.24 | 4.37 | 3.14 | 0.86 | 0.89 |
| 41 | 3338 | 0.85 | −19.6 | 4.05 | 2.89 | 0.80 | 0.82 |
| 42 | 2953 | 0.77 | −20.17 | 5.11 | 3.43 | 1.00 | 0.97 |
| 43 | 2950 | 0.88 | −18.3 | 3.18 | 2.12 | 0.62 | 0.60 |
| 44 | 2848 | 0.85 | −22.64 | 5.18 | 2.64 | 1.02 | 0.75 |
| 45 | 2815 | 0.73 | −18.86 | 4.15 | 2.98 | 0.81 | 0.84 |

*The truncated expansion of the excess entropy used can merely include the first order terms. The first order excess entropic term for all neat fluids is strictly zero, however the second order and larger terms will be quite large.

TABLE 8

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1H1P:CMG | | 1H1S:4SP | | −4.53 | −4.05 | −4.17 |
| 1KE9:LS5 | | 1KE5:LS1 | | −0.1 | −0.47 | −0.38 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1KE8:LS4 | 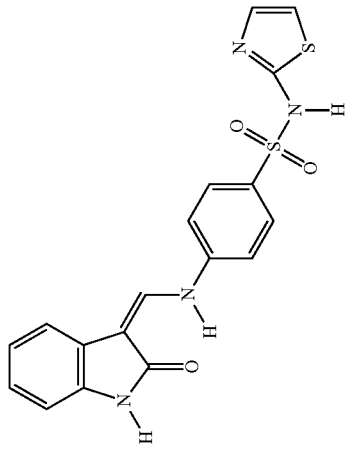 | 1KE5:LS1 | 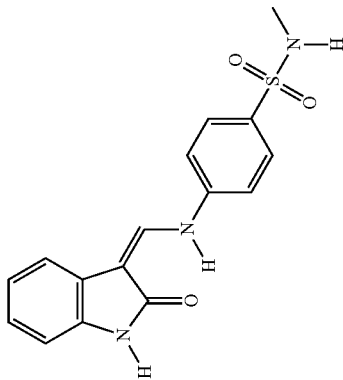 | −0.35 | −0.30 | −0.24 |
| 1OGU:8a | 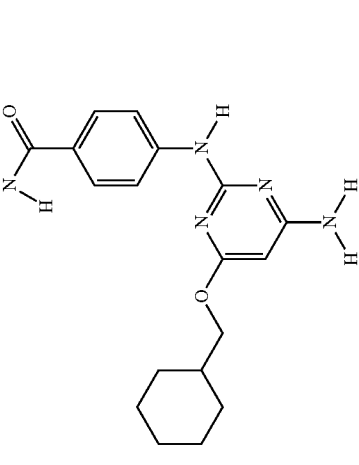 | 1OGU:ST8 | 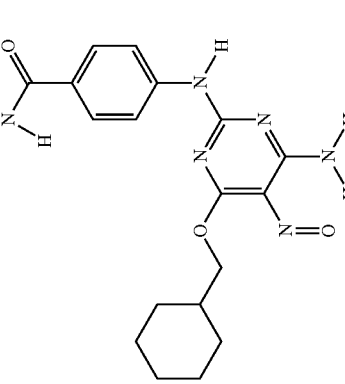 | −4.45 | −2.33 | −1.97 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1OIU:N76 | | 1OIY:N41 | | −0.71 | −0.51 | 0.05 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1OI9:2 | 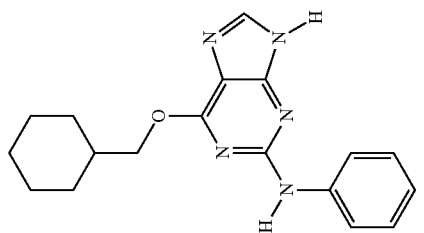 | 1OIY:N41 | 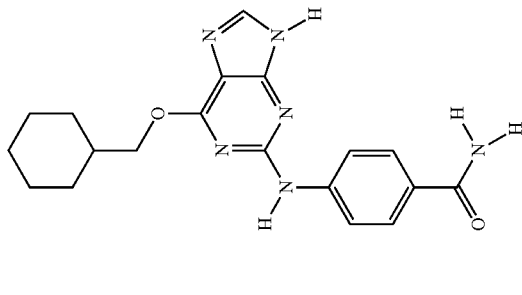 | −1.62 | −0.70 | −0.75 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1OIU:N76 | | 1OI9:N20 | | −0.66 | −0.21 | 0.31 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1OI9:2 | 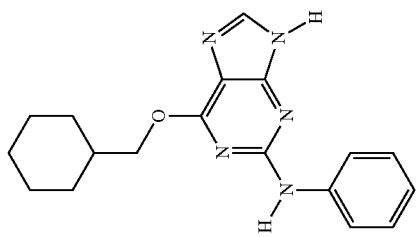 | 1OI9:N20 | 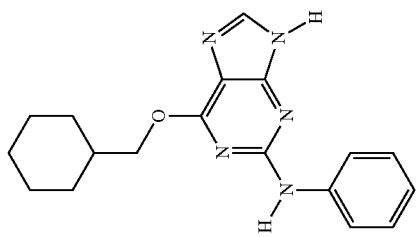 | −1.58 | −0.40 | −0.49 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1OI9:2 | | 1OIU:N76 | | −0.91 | −0.19 | −0.80 |
| 1PXJ:CK2 | | 1PXL:CK4 | | −1.59 | −2.22 | −2.02 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1PXI:CK2 | 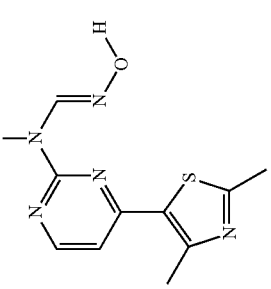 | 1PXK:CK3 | 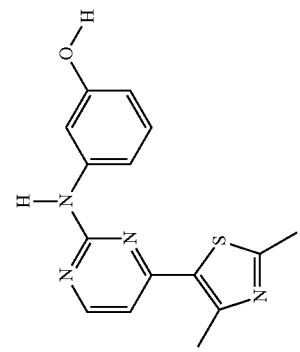 | −1.06 | −0.95 | −0.66 |
| 1PXM:i1 | 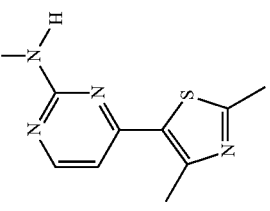 | 1PXM:CK5 | 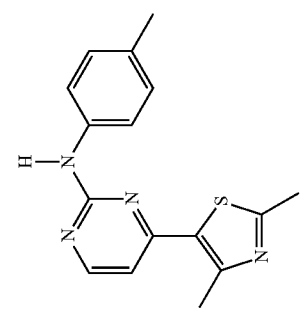 | −0.17 | −0.21 | −0.24 |
| 1PXP:CK8 | 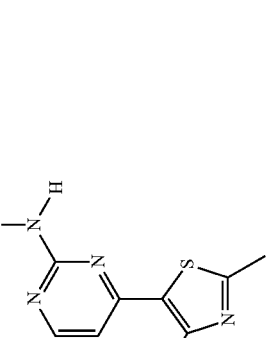 | 1PXM:CK5 | 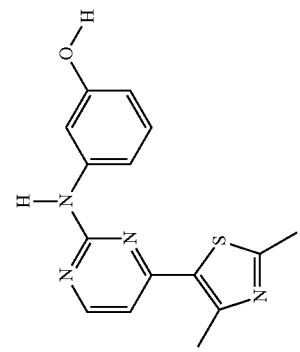 | −0.77 | −0.25 | −0.60 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1PXP:CK8 | 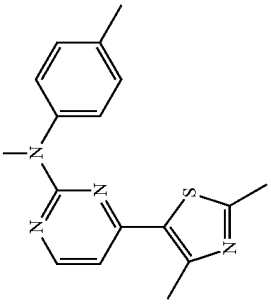 | 1PXM:11 | 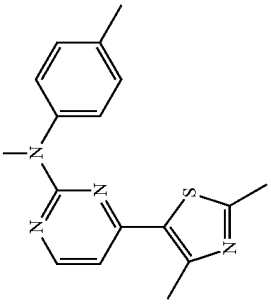 | −0.6 | −0.05 | −0.36 |
| 1VYZ:N5B | 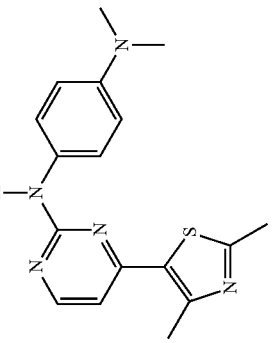 | 1VYW:292 | 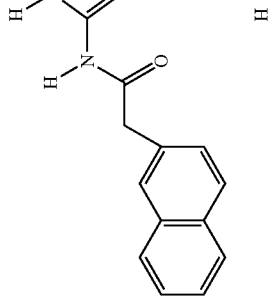 | −1.23 | 0.80 | 0.65 |
| 1VYZ:1 | 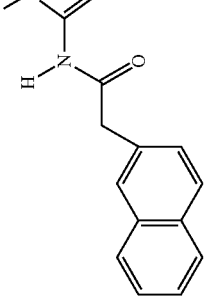 | 1VYW:292 | | −2.21 | −2.23 | −1.94 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 1VYZ:1 | | 1VYZ:N5B | | −0.98 | −3.03 | −2.59 |
| 2B52:D42 | | 2B52:8i | | −0.41 | 0.34 | 0.19 |
| 2B53:14 | | 2B53:D23 | | −0.55 | −1.74 | −1.83 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb idx)(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B53:42 | | 2B53:D23 | | −0.65 | −0.38 | −0.25 |
| 2B53:42 | | 2B53:14 | | −0.11 | 1.35 | 1.58 |
| 2B54:19m | | 2B54:22g | | −0.08 | 0.00 | 0.00 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:D05 | | 2B54:22g | | −0.21 | 0.00 | 0.00 |
| 2B54:18i | | 2B54:22g | | −0.32 | 0.00 | 0.00 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:18b | 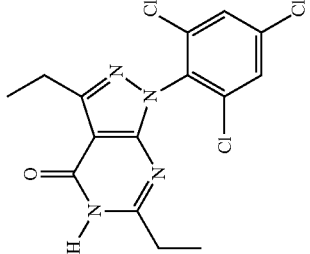 | 2B54:22g | 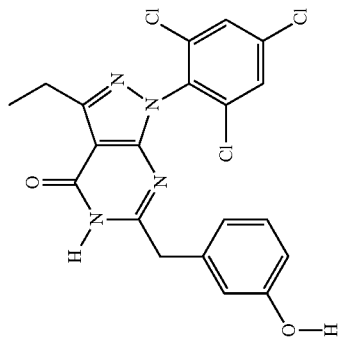 | −1.15 | −0.28 | −0.96 |
| 2B54:10i | 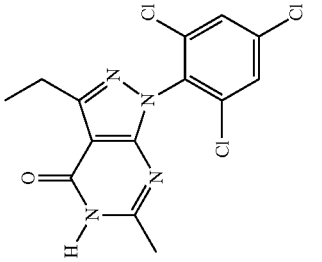 | 2B54:22g | 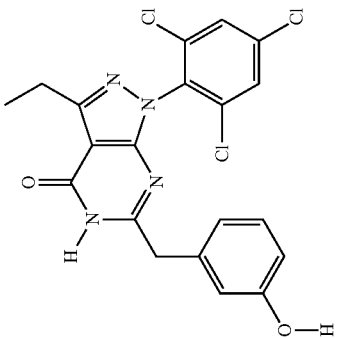 | −1.37 | −0.48 | −1.02 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:D05 | | 2B54:19m | | −0.13 | 0.00 | 0.00 |
| 2B54:18i | | 2B54:19m | | −0.24 | 0.00 | 0.00 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:18b | | 2B54:19m | | −1.07 | −0.28 | −0.96 |
| 2B54:10i | | 2B54:19m | | −1.29 | −0.48 | −1.02 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:18i | | 2B54:D05 | | −0.11 | 0.00 | 0.00 |
| 2B54:18b | | 2B54:D05 | | −0.94 | −0.28 | −0.96 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:10i | | 2B54:D05 | | −1.16 | −0.48 | −1.02 |
| 2B54:18b | | 2B54:18i | | −0.83 | −0.28 | −0.96 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2B54:10i | | 2B54:18i | | −1.05 | −0.48 | −1.02 |
| 2B54:10i | | 2B54:18b | | −0.22 | −0.20 | −0.06 |
| 2BHE:1 | | 2BHE:BRY | | −0.41 | −0.43 | −0.30 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id)x(ligand residue name)"; and when the ligand was built from congeneric series data, the ligand was designated "(pdb id)x(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2BKZ:7h | 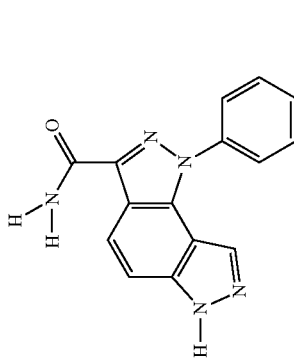 | 2BKZ:SBC | 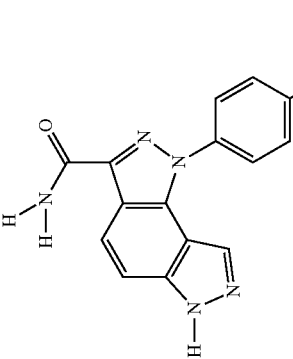 | -2.16 | -1.08 | -0.98 |
| 2BKZ:7x | 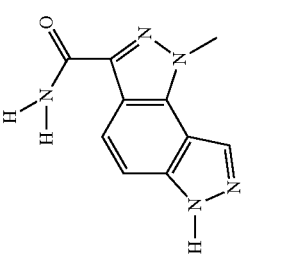 | 2BKZ:SBC | 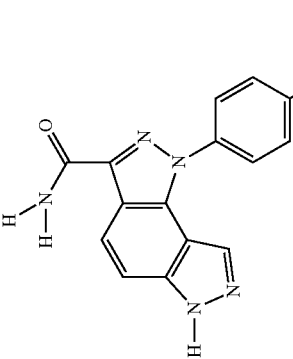 | -2.55 | -1.71 | -1.87 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2BKZ:7x | 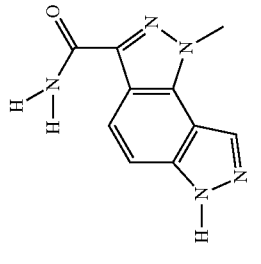 | 2BKZ:7h | 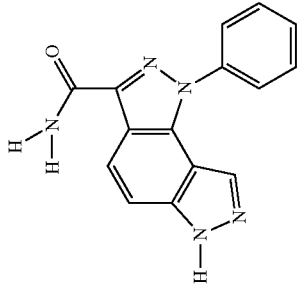 | −0.39 | −0.62 | −0.88 |
| 2CLX:1b | 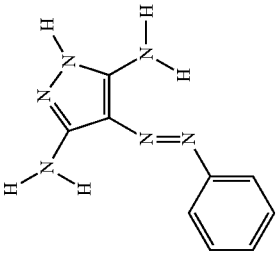 | 2CLX:F18 | 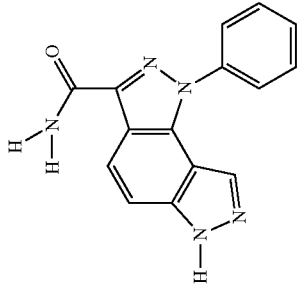 | −0.96 | −0.99 | −0.77 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2FVD:35 | | 2FVD:LIA | | −0.51 | 0.00 | 0.00 |
| 2FVD:37 | | 2FVD:LIA | | −0.87 | −0.07 | 0.00 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2FVD:29 | | 2FVD:LIA | | −1.24 | −0.07 | 0.00 |
| 2FVD:37 | | 2FVD:35 | | −0.37 | −0.07 | 0.00 |

TABLE 8-continued

Inhibition data for the congeneric ligand pairs binding to CDK2 and the predicted activity differences from the trained 3-parameter and 5-parameter displaced-solvent functionals. When a ligand was taken from a solved crystal structure, the ligand was designated "(pdb id):(ligand residue name)"; and when the ligand was built from congeneric series data, the ligand was designated "(template pdb id):(molecule number in the reporting publication)".

| Initial Ligand | Initial Ligand Structure | Final Ligand | Final Ligand Structure | $\Delta\Delta G_{exp}$ (kcal/mol) | $\Delta\Delta G_{3p}$ (kcal/mol) | $\Delta\Delta G_{5p}$ (kcal/mol) |
|---|---|---|---|---|---|---|
| 2FVD:29 | | 2FVD:35 | | −0.73 | −0.07 | 0.00 |
| 2FVD:29 | | 2FVD:37 | | −0.37 | 0.00 | 0.00 |

TABLE 9

The optimized parameters for the 3-parameter and 5-parameter forms of the displaced-solvent functional trained to reproduce the experimentally measured differences in binding affinity of 47 CDK2 congeneric pairs.

| Parameters: | $R_{co}$ (Å) | $E_{rwd}$ (kcal/mol) | $-TS_{rwd}$ (kcal/mol) | $E_{co}$ (kcal/mol) | $TS_{co}$ (kcal/mol) |
|---|---|---|---|---|---|
| version 3p | 2.8 | −0.59 | −0.59 | −19.17 | 1.97 |
| version 5p | 2.23 | −0.54 | −0.81 | −19.54 | 1.95 |

TABLE 10

The optimized parameters for the 3-parameter and 5-parameter forms of the displaced-solvent functional trained to reproduce the experimentally measured differences in binding affinity of 31 fXa and 47 CDK2 congeneric pairs.

| Parameters: | $R_{co}/$ (Å) | $E_{rwd}/$(kcal/mol) | $-TS_{rwd}/$ (kcal/mol) | $E_{co}/$ (kcal/mol) | $TS_{co}/$ (kcal/mol) |
|---|---|---|---|---|---|
| version 3p | 2.8 | −0.95 | −0.95 | −18.22 | 1.66 |
| version 5p | 2.91 | −1.33 | −0.64 | −18.58 | 1.71 |

The foregoing merely illustrates the principles of the disclosed subject matter. Various modifications and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope thereof.

What is claimed is:

1. A method of computing a binding affinity of a ligand for a receptor, comprising:
   (a) calculating local statistical thermodynamic properties of water molecules solvating the receptor, wherein the calculating comprises using a computer processor; and
   (b) calculating free energy gain of displacement of solvent from the receptor by the ligand including:
      (i) inserting the ligand into the receptor,
      (ii) algorithmically determining steric overlap of the ligand with the solvent, and
      (iii) calculating the free energy gain of the ligand sterically displacing the solvent based on the results of the algorithmically determining steric overlap of the ligand with the solvent and the thermodynamic properties of the displaced solvent.

2. The method of claim 1, wherein calculating local statistical thermodynamic properties of water molecules solvating the receptor comprises:
   (c) sampling configurations of the water molecules solvating a receptor;
   (d) extracting thermodynamic information about the solvating water molecules from the configurations including:
      (i) automatically partitioning observed water molecules configurations into hydration sites,
      (ii) computing average system interaction energies of water molecules occupying the hydration sites, and
      (iii) computing excess entropies of the water molecules occupying the hydration sites.

3. The method of claim 1, wherein the free energy gain for atoms of the ligand sterically displacing the solvent is computed as a function of the thermodynamic properties of the solvent.

4. The method of claim 3, wherein the free energy gain for atoms of the ligand sterically displacing the solvent is the excess chemical potential of the solvent as compared to bulk fluid.

5. The method of claim 3, wherein enthalpic contribution to the free energy of a ligand atom displacing a hydration site is assigned as a constant where a value of the average system interaction energy exceeds a threshold.

6. The method of claim 5, wherein the parameters of constant gains upon displacement and threshold values are determined by optimizing against experimental data.

7. The method of claim 6, wherein values for a particular receptor are optimized by using data for ligands binding to that receptor.

8. The method of claim 6, wherein values for a class of receptors are optimized by fitting to data from a diverse set of receptor-ligand complexes.

9. The method of claim 3, wherein entropic contribution to the free energy of a ligand atom displacing a hydration site is assigned as a constant where a value of the excess entropy exceeds a specified threshold.

10. The method of claim 1, wherein the free energy gain is computed as the sum of (1) the output of the function of the thermodynamic properties of the solvent and (2) the excess chemical potential of the solvent as compared to bulk fluid.

11. The method of claim 1, wherein the free energy gain is computed as the sum of the enthalpic and entropic contribution of a ligand atom displacing a hydration site.

12. The method of claim 1, further comprising:
   (e) calculating a difference in binding free energy between two ligands, the difference corresponding to the difference in the free energy gain from water displacement.

13. The method of claim 12, wherein the ligands are a congeneric pair.

14. The method of claim 13, wherein the ligands differ by deletions of atoms.

* * * * *

UNITED STATES PATENT AND TRADEMARK OFFICE
CERTIFICATE OF CORRECTION

| | | |
|---|---|---|
| PATENT NO. | : 7,970,581 B2 | Page 1 of 1 |
| APPLICATION NO. | : 12/791493 | |
| DATED | : June 28, 2011 | |
| INVENTOR(S) | : Thomas Young et al. | |

It is certified that error appears in the above-identified patent and that said Letters Patent is hereby corrected as shown below:

In the Specifications:

Column 1, lines 16-23:
STATEMENT REGARDING FEDERALLY SPONSORED RESEARCH
The subject matter described herein was funded in part by federal grants: subcontract NIH GM52018, NIH GM43340, UMD UMARY Z477901, and NSF CHE 06 13401. The United States Government may have certain rights herein.

should read

--STATEMENT REGARDING FEDERALLY SPONSORED RESEARCH OR DEVELOPMENT
This invention was made with government support under grant numbers GM52018 and GM43340 awarded by the National Institutes of Health and CHE0613401 awarded by the National Science Foundation. The government has certain rights in the invention.--

Signed and Sealed this
Fourteenth Day of May, 2013

Teresa Stanek Rea
*Acting Director of the United States Patent and Trademark Office*